(12) United States Patent
Beck et al.

(10) Patent No.: US 9,309,272 B2
(45) Date of Patent: Apr. 12, 2016

(54) METAL OXIDE PARTICLES AFTERTREATED WITH ORGANIC PHOSPHORUS COMPOUNDS

(71) Applicants: MERCK PATENT GMBH, Darmstadt (DE); SACHTLEBEN CHEMIE GMBH, Duisburg (DE)

(72) Inventors: Joern Beck, Seeheim-Jugenheim (DE); Ruediger Graf, Otzberg (DE); Frank Pfluecker, Darmstadt (DE); Gabriele Benkner, Moers (DE); Bernd Hirthe, Toenisvorst (DE); Stephan John, Duisburg (DE)

(73) Assignees: MERCK PATENT GMBH, Darmstadt (DE); SACHTLEBEN CHEMIE GMBH, Duisburg (DE)

( * ) Notice: Subject to any disclaimer, the term of this patent is extended or adjusted under 35 U.S.C. 154(b) by 0 days.

(21) Appl. No.: 14/484,373

(22) Filed: Sep. 12, 2014

(65) Prior Publication Data
US 2015/0010602 A1  Jan. 8, 2015

Related U.S. Application Data

(62) Division of application No. 13/637,177, filed as application No. PCT/EP2011/000967 on Feb. 28, 2011, now Pat. No. 8,883,215.

(30) Foreign Application Priority Data

Mar. 26, 2010 (EP) .................................. 10003251

(51) Int. Cl.
| | | |
|---|---|---|
| A61K 9/14 | (2006.01) |
| C07F 7/28 | (2006.01) |
| A61K 9/50 | (2006.01) |
| B01J 13/20 | (2006.01) |
| A61K 8/02 | (2006.01) |
| A61K 8/24 | (2006.01) |
| A61K 8/29 | (2006.01) |
| A61K 8/35 | (2006.01) |
| A61Q 17/04 | (2006.01) |
| A61Q 19/04 | (2006.01) |
| B82Y 30/00 | (2011.01) |
| C09C 1/36 | (2006.01) |
| C07C 45/86 | (2006.01) |

(52) U.S. Cl.
CPC ................. *C07F 7/28* (2013.01); *A61K 8/0241* (2013.01); *A61K 8/24* (2013.01); *A61K 8/29* (2013.01); *A61K 8/35* (2013.01); *A61K 9/50* (2013.01); *A61Q 17/04* (2013.01); *A61Q 19/04* (2013.01); *B01J 13/20* (2013.01); *B82Y 30/00* (2013.01); *C07C 45/86* (2013.01); *C09C 1/3669* (2013.01); *A61K 2800/413* (2013.01); *A61K 2800/52* (2013.01); *A61K 2800/621* (2013.01); *C01P 2004/64* (2013.01); *Y10T 428/2982* (2015.01)

(58) Field of Classification Search
CPC ....... B01J 13/20; C01P 2004/64; B82Y 30/00
See application file for complete search history.

(56) References Cited

U.S. PATENT DOCUMENTS

| | | | |
|---|---|---|---|
| 4,857,308 A | 8/1989 | Fukasawa et al. |
| 5,837,049 A | 11/1998 | Watson et al. |
| 7,138,010 B1 | 11/2006 | El-Shoubary et al. |

FOREIGN PATENT DOCUMENTS

| | | |
|---|---|---|
| EP | 0154150 | 9/1985 |
| EP | 0707051 | 4/1996 |
| WO | 0242381 | 5/2002 |
| WO | 02051945 | 7/2002 |
| WO | 2007070204 | 6/2007 |

*Primary Examiner* — Carlos Azpuru
(74) *Attorney, Agent, or Firm* — Millen White Zelano and Branigan, PC; John Sopp; Anthony Zelano

(57) ABSTRACT

The invention relates to metal oxide particles and/or metal hydroxide particles, aftertreated with an organic phosphorus compound, process for the preparation thereof, and compositions comprising same.

16 Claims, No Drawings

METAL OXIDE PARTICLES AFTERTREATED WITH ORGANIC PHOSPHORUS COMPOUNDS

The invention relates to metal oxide particles and/or metal hydroxide particles, aftertreated with an organic phosphorus compound, production and use thereof.

The present invention furthermore relates to novel compositions for topical application which comprise, in particular, the self-tanning agent dihydroxyacetone in combination with the metal oxide/metal hydroxide particles according to the invention for the protection of the skin and/or hair against UV radiation. Particularly preferred metal oxide particles are titanium dioxide particles.

Dihydroxyacetone (DHA) has been employed for many years as self-tanning agent in cosmetics. In recent years, there has also been an increased trend to combine self-tanning products with UV filters, for example for day care. However, this was only possible to a limited extent in the past since DHA exhibits strong degradation during storage in combination with conventional inorganic UV filters, in particular $TiO_2$.

Conventional micronised titanium dioxide particles are aftertreated with inorganic oxides or hydroxides of the elements Al, Si, Zr, Ce and Fe in order to reduce the photocatalytic activity. Aftertreatment with $Al_2O_3$ proves to be particularly suitable here. Besides the photocatalytic activity, which results in degradation or destruction of the surrounding matrix on use of these products, further undesired effects arise, in particular, in cosmetic formulations:
- degradation of DHA if it is combined with $TiO_2$ in formulations
- colour reactions of the $TiO_2$ particles with DHA and with further organic molecules in the composition
- greying of the formulations on UV irradiation.

Some of these effects, for example the greying or colour reactions with, for example, ascorbyl palmitate, can be reduced by diverse aftertreatments of the titanium dioxide particles, for example achieved by the qualities of the commercial products Parsol® TX from DSM or UV-TITAN M263 from Sachtleben.

Parsol® TX is a white powder consisting of titanium dioxide of the rutile crystal structure having a $TiO_2$ content of 82.0 to 87.0 percent by weight, with an $SiO_2$ coating having an $SiO_2$ content of 10.5 to 14.5 percent by weight and a dimethicone coating.

UV-TITAN M263 is a white powder consisting of titanium dioxide (88%) with an inorganic constituent of 7% of aluminium phosphate and an organic constituent of 3% of polyvinylpyrrolidone (INCI of the product: Titanium Dioxide, Alumina, Sodium Hexametaphosphate, Polyvinylpyrrolidone).

However, it has been found that even known conventional micronised titanium dioxide particles, as described above, which are provided with diverse aftertreatments, such as $SiO_2$ and/or further aftertreatments, and exhibit this good photocatalytic stability and/or low reactivities with other organic molecules, these are not automatically also compatible with dihydroxyacetone.

The object of the invention therefore lies in the provision of metal oxide particles and/or metal hydroxide particles, in particular of titanium dioxide particles, which are compatible with dihydroxyacetone or dihydroxyacetone derivatives, in particular with dihydroxyacetone.

Surprisingly, it has now been found that it is possible to employ certain metal oxide particles and/or metal hydroxide particles, in particular titanium dioxide particles, as UV protection agents, in cosmetic formulations which comprise dihydroxyacetone and at the same time to reduce or prevent the degradation of the dihydroxyacetone in the cosmetic formulations. The degradation of dihydroxyacetone in the cosmetic composition is, in particular, less compared with cosmetic compositions comprising dihydroxyacetone and particles which have an identical structure, but no aftertreatment according to the invention. The degradation of dihydroxyacetone in a cosmetic composition comprising the particles according to the invention and dihydroxyacetone is, for example, less compared with cosmetic compositions comprising dihydroxyacetone and commercially available known titanium dioxide UV protection agents. It has furthermore been found that the preferred titanium dioxide particles according to the invention also have the property of substantially preventing colour reactions of titanium dioxide with organic compounds, with the photocatalytic activity and the greying stability remaining comparable with known titanium dioxide UV protection agents.

The object is achieved by an aftercoating of the metal oxide particles and/or metal hydroxide particles, in particular by an aftercoating of titanium dioxide base particles, with a specific organic phosphorus compound.

The invention therefore relates to metal oxide particles and/or metal hydroxide particles having a primary particle size according to the Scherrer method in the range from 5 nm to 100 nm, aftertreated with an organic phosphorus compound selected from the group of the hydroxyalkyldiphosphonic acids, alkylphosphonic acids, which may be substituted by at least one COOH group, aminoalkylenephosphonic acids or organic phosphoric acid esters or salts thereof.

The product obtained is preferably characterised by a water content of greater than 1.5% by weight. The water content can be determined, for example, by Karl Fischer titration, as described in Eugen Scholz, Karl-Fischer-Titration [Karl Fischer Titration], Springer-Verlag 1984.

JP 2950495 discloses paints comprising titanium dioxide particles, where the titanium dioxide particles have been aftertreated with an organic phosphoric acid ester. However, titanium dioxide particles having an average particle size between 150 to 400 nm were used here, i.e. pigments which are suitable for paints. According to the teaching of JP 2950495, the aftertreated titanium dioxide particles in the paint cause an improvement in the water-repellent properties of the paint film. JP 2950495 contains neither the teaching of the general aftertreatment of titanium dioxide particles having a smaller size, nor a prospect that the pigments according to the invention would be relevant for cosmetics.

EP 154150 describes a make-up cosmetic or a body cosmetic comprising inorganic filler pigments and composite pigments aftertreated with a dialkyl phosphate containing alkyl groups having 14 to 22 C atoms, which enable the cosmetic to have an improved water repulsion capacity and improved softness on the skin. Inorganic filler pigments used are talc, sericite, mica aftertreated with titanium dioxide. Particles according to the invention, in particular titanium dioxide particles according to the invention, are not described.

In accordance with the invention, the organic phosphorus compound is applied in an amount of 5 to 50 percent by weight, preferably from 5 to 20 percent by weight, particularly preferably from 6 to 15 percent by weight. Very particularly preferably, an organic phosphoric acid monoalkyl ester is applied in an amount of 6 to 9 percent by weight.

The content of organic phosphorus compound is determined by determination of the organic carbon. To this end, the sample is burned at 1300° C. in a stream of oxygen, and the carbon dioxide formed is detected by infrared analysis. The measurement is carried out, for example, using the Eltra CS580 automatic CS analyser. The precise method description is given in the experimental part.

The metal oxide and/or hydroxide for the particles according to the invention can be selected from the group of the oxides and hydroxides of silicon, titanium, zinc, aluminium, cerium, iron, yttrium or zirconium or mixtures thereof. These metal oxides and/or metal hydroxides form the base particle which is aftertreated at least with the organic phosphorus compound.

The metal oxide and/or metal hydroxide is preferably selected from the group of the oxides and hydroxides of silicon, titanium or zinc. Particularly preferred particles according to the invention are titanium dioxide particles.

Before aftertreatment with the organic phosphorus compound, the base particles may have been provided with at least one further coating, which comprise, for example, metal oxides or hydroxides of silicon, titanium, zinc, aluminium, cerium, iron, yttrium, manganese or zirconium, where the metal is preferably selected differently to the metal of the base particle. The further coating may also comprise organic acids selected from the group stearic acid, lauric acid, caproic acid or palmitic acid, polyols, polymers or organosilicone compounds.

Polyols are, for example, the compounds glycerol, sorbitol, propylene glycol, pentanediol, hexanediol, ethylhexylglycerol, pentaerythritol, dipentaerythritol or trimethylolpropane. An organosilicone compound is, for example, octyltrimethylsilane, methicone, dimethicone (=triethoxycaprylsilane), trimethoxycaprylsilane, dimethicone/methicone copolymer, diphenyl capryl methicone, polymethyl methacrylate dimethicone or simethicone. Polymers are, for example, polyvinylpyrrolidone (PVP) or polyethylene (PE).

It may be advantageous to pretreat the base particle with aluminium hydroxide or oxide/dioxide and/or silicon hydroxide or oxide/dioxide and/or manganese oxide/hydroxide, preferably with silicon hydroxide or oxide/dioxide and manganese oxide/hydroxide or silicon hydroxide or oxide/dioxide, particularly preferably with silicon hydroxide or oxide/dioxide, before the aftertreatment with an organic phosphorus compound.

In a preferred embodiment of the particles according to the invention, in particular of the particularly preferred titanium dioxide particles, a further coating comprising aluminium hydroxide or oxide/dioxide and/or silicon hydroxide or oxide/dioxide and/or manganese oxide/hydroxide, preferably silicon hydroxide or oxide/dioxide and manganese oxide/hydroxide or silicon hydroxide or oxide/dioxide, particularly preferably silicon hydroxide or oxide/dioxide, which may optionally also comprise further coatings, as described above, is applied in addition to the aftertreatment with an organic phosphorus compound. The content of aluminium hydroxide or oxide/dioxide and/or silicon hydroxide or oxide/dioxide is, for example, in the range from 5 to 60 percent by weight, preferably in the range from 8 to 45 percent by weight, particularly preferably in the range from 10 to 35 percent by weight, based on the $TiO_2$ content of the particles to be coated, and this is followed by the aftertreatment with an organic phosphorus compound. The content of the manganese-containing layer, in particular the content of manganese dioxide and/or manganese hydroxide, based on the particle as a whole, is 0.1% by weight to 1% by weight, preferably 0.2% by weight to 0.7% by weight and particularly preferably 0.2% by weight or 0.5% by weight.

The base particle, in particular the titanium dioxide base particle, is preferably treated with silicon hydroxide or oxide/dioxide, as described above. The coating with silicon hydroxide or oxide/dioxide is also referred to below as silicon dioxide coating.

The $SiO_2$ content of the silicon hydroxide or oxide/dioxide coating is determined based on ICP-OES. The variation latitude of the $SiO_2$ content values obtained is in the indicated range from 25 to 45 percent by weight, based on the titanium dioxide, plus/minus 0.25%.

ICP-OES stands for inductively coupled plasma optical emission spectrometry. The measurement is carried out using the Perkin Elmer Optima 3300DV instrument, using the method described in the experimental part of the description under the $SiO_2$ determination example.

The silicon dioxide coating is intended to cover the base particles or in other words the particulate metal oxide and/or metal hydroxide, in particular the nanoparticulate metal oxide and/or metal hydroxide, as completely as possible.

The titanium dioxide base particle is therefore very particularly preferably provided firstly with a silicon coating, where the content of silicon hydroxide or oxide/dioxide is in the range from 20 to 35 percent by weight, based on the $TiO_2$ content of the particles to be coated, and the aftertreatment with an organic phosphorus compound, as described below or described as preferred below, is then carried out. The content of silicon hydroxide or oxide/dioxide is preferably 20 or 35 percent by weight.

The particles described, in particular the titanium dioxide particles, have a primary particle size according to the Scherrer method in the range from 5 nm to 100 nm, preferably in the range 8 to 50 nm and particularly preferably below 25 nm. The dimensions of the nanoparticulate titanium dioxide according to the invention, which can be determined in a transmission electron microscope, are usually a length of 10 to 100 nm and a width of 5 to 70 nm. The length is preferably in the range from 30 to 70 nm and the width in the range from 10 to 40 nm.

Nanoparticles in the sense of the invention are particles whose three dimensions are in the nano region, i.e. <100 nm. These are the three dimensions of the primary particles.

Aggregates in the sense of the invention are an aggregation of primary particles, by chemical or physical bonding, where the external surface area is significantly smaller than the sum of the calculated surface areas of the individual particles, i.e. the primary particles. Aggregates in the sense of the invention have dimensions of 30 nm to 150 nm.

Agglomerates in the sense of the invention are an agglomeration of primary particles or/and aggregates, by chemical or physical bonding, where the external surface area is not significantly smaller than the sum of the calculated surface areas of the individual particles, but where the dimensions are in ranges between 0.1 μm and 100 μm.

The term titanium dioxide particles therefore encompasses both the primary particles and also aggregates or agglomerates. In the course of grinding, the size of the aggregations of the primary particles can be adjusted to the desired size for use in the respective application.

In a particularly preferred embodiment of the particles according to the invention, in particular of the titanium dioxide particles, a base particle which has been hydrothermally treated in advance is employed.

Hydrothermal treatment refers to the heating of an aqueous solution, or suspension or dispersion in a closed container, optionally under pressure (cf. also Ullmanns Enzyklopädie der Technischen Chemie [Ullmann's Encyclopaedia of Industrial Chemistry], 4th Edition, 1978, Volume 15, pp. 117 ff: K. Recker, Monocrystal Cultivation).

The hydrothermal treatment of the base particles is preferably carried out at temperatures in the range from 40 to 360° C., preferably in the range from 80 to 220° C. and particularly preferably in the range from 140 to 200° C.

The hydrothermal treatment results in the formation of stable nanocrystal-lites of uniform size and shape. At low temperatures, "needle-shaped" crystallites form. With increasing temperature, the crystallites become rounded. Oval shapes form, which turn into round particles at very high temperatures. In addition, uniform crystal growth occurs.

Advantages of hydrothermal treatment compared with conventional thermal treatment (temperature treatment of a dried powder) are:
  formation of uniform crystallite sizes having a narrow particle-size distribution
  prevention of sinter effects (formation of undesired aggregates).

Titanium dioxide here can be in the form of rutile or anatase or in amorphous form, but preferably in the form of rutile and/or anatase. Preferred primary particle size of the titanium dioxide base particles is in the range from 5 to 50 nm. These primary particles, in particular in the case of anatase, are preferably round, while rutile primary particles frequently occur in needle or spindle form as far as ovals ("egg-shaped"). However, round rutile primary particles can also be employed in accordance with the invention.

Titanium dioxide base particles can be produced by conventional methods which are familiar to the person skilled in the art, preferably by wet-chemical methods.

Base particles of the metals silicon, zinc, aluminium, cerium, iron, yttrium, manganese or zirconium can be produced by conventional methods which are familiar to the person skilled in the art, preferably by wet-chemical methods. Many base particles are commercially available.

In order to reduce the photocatalytic activity and in order to reduce the greying of cosmetic formulations or in order to enhance the antioxidative properties, the titanium dioxide base particle may be doped with suitable elements, for example iron or manganese. An iron-doped titanium dioxide base particle is particularly preferably used.

The organic phosphorus compound is selected from the group of the hydroxyalkyldiphosphonic acids or salts thereof, alkylphosphonic acids, which may be substituted by at least one COOH group, or salts thereof, aminoalkylenephosphonic acids or salts thereof or organic phosphoric acid esters or salts thereof.

Preference is given to the use of the corresponding phosphonic acids or the organic phosphoric acid esters.

Hydroxyalkyldiphosphonic acids are, for example, compounds of the formula I, where R denotes a linear or branched alkyl group having 1 to 20 C atoms.

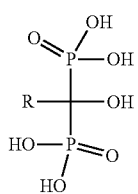

I

The $C_1$-$C_{20}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl, dodecyl, tridecyl, tetradecyl, pentadecyl, hexadecyl, heptadecyl, octadecyl, nonadecyl or eicosyl.

Preferred compounds of the formula I are 1-hydroxyethane-1,1-diphosphonic acid or 1-hydroxydodecane-1,1-diphosphonic acid. 1-Hydroxyethane-1,1-diphosphonic acid is commercially available under the name Cublen® K 60 from Zschimmer & Schwarz. 1-Hydroxydodecane-1,1-diphosphonic acid is present, for example, in the commercial product Tensan AO from Polygon Chemie (75%).

Preferred salts of the hydroxyalkyldiphosphonic acids, so-called hydroxy-alkyldiphosphonates, are alkali or alkaline-earth metal salts of the compounds of the formula I, as described above, in particular sodium or potassium salts.

Alkylphosphonic acids, which may be substituted by at least one COOH group, are, for example, alkylphosphonic acids containing an alkyl group containing a linear or branched alkyl group having 1 to 20 C atoms, which may optionally be replaced by at least one COOH group. Preferred alkylphosphonic acids are, for example, laurylphosphonic acid or octylphosphonic acid, which are commercially available from Rhodia. A preferred alkylphosphonic acid containing at least one COOH group is, for example, 2-phosphonobutane-1,2,4-tricarboxylic acid, which is available from Zschimmer & Schwarz under the trade name Cublen® P 50.

Preferred salts of the alkylphosphonic acids, as described above, are alkali or alkaline-earth metal salts, in particular sodium or potassium salts.

Aminoalkylenephosphonic acids are, for example, compounds of the formula II,

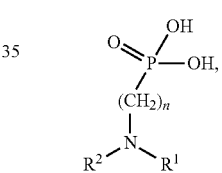

II where n denotes 1, 2, 3 or 4, preferably 1 or 2, and
$R^1$ and $R^2$ each, independently of one another, stand for
—$(CH_2)_{n1}$—$P(O)(OH)_2$ or —$(CH_2)_{n1}$—$N\{[(CH_2)_{n2}$—$P(O)(OH)_2][(CH_2)_{n3}$—$P(O)(OH)_2]\}$, where n1, n2 or n3 each independently denote 1, 2, 3 or 4, preferably 1 or 2.

Preferred compounds of the formula II are aminotrimethylenephosphonic acid, diethylenetriaminepenta(methylenephosphonic acid) or ethylenediaminetetra(methylenephosphonic acid). Aminotrimethylenephosphonic acid is, for example, commercially available under the trade name Cublen® AP 5.

Preferred salts of the aminoalkylenephosphonic acids are alkali or alkaline-earth metal salts of the compounds of the formula II, as described above, in particular sodium or potassium salts.

Organic phosphoric acid esters are, for example, phosphoric acid monoalkyl esters containing a linear or branched alkyl group having 1 to 20 C atoms, phosphoric acid dialkyl esters containing linear or branched alkyl groups having 1 to 20 C atoms, which are each selected independently of one another, phosphoric acid trialkyl esters containing linear or branched alkyl groups having 1 to 20 C atoms, which are each selected independently of one another, salts of the phosphoric acid monoalkyl esters or phosphoric acid dialkyl esters or mixtures of the said phosphoric acid esters, phosphoric acid oxyesters, phosphoric acid mixed esters or nucleotides. It is also possible to use mixtures of phosphoric acid monoalkyl esters and phosphoric acid dialkyl esters.

Phosphoric acid monoalkyl esters are, for example, phosphoric acid monomethyl ester, phosphoric acid monoethyl ester, phosphoric acid monooctyl ester, phosphoric acid monocetyl ester, phosphoric acid monostearyl ester or phosphoric acid monododecyl ester. Phosphoric acid monodecyl ester is, for example, commercially available under the name Hostaphat® CC100 from Clariant. A mixture of phosphoric acid mono- and distearyl esters is commercially available under the name Hostaphat® CS120 or Amphisol® A from DSM.

The alkyl groups of the di- or trialkyl esters of phosphoric acid may be identical or different. They are preferably identical. Selected di- or trialkyl esters are, for example, phosphoric acid dimethyl ester, phosphoric acid trimethyl ester, phosphoric acid diethyl ester, phosphoric acid triethyl ester, phosphoric acid dioctyl ester, phosphoric acid trioctyl ester, phosphoric acid dicetyl ester, phosphoric acid distearyl ester or phosphoric acid didodecyl ester.

Preferred salts of the phosphoric acid monoalkyl esters or phosphoric acid dialkyl esters are alkali or alkaline-earth metal salts, in particular sodium or potassium salts. Potassium cetyl phosphate is, for example, available under the trade name Amphisol® K from DSM.

Phosphoric acid oxyesters are, for example, phosphoric acid ascorbyl ester or alkyltetraglycol ether phosphoric acid esters.

A phosphoric acid mixed ester is, for example, 3-aminopropyl tocopheryl phosphoric acid ester.

Nucleotides which can be employed in accordance with the invention are, for example, adenosine 5-monophosphate (AMP), adenosine 3,5-cyclo-phosphate (c-AMP), adenosine diphosphate (ADP) or adenosine triphosphate (ATP).

Particular preference is given to the use of phosphoric acid monoalkyl esters, as described above. The use of phosphoric acid monocetyl ester is particularly preferred.

A process for the production of the particles according to the invention is, for example, characterised in that a stirrable dispersion of a metal oxide base particle and/or a metal hydroxide base body is heated, the organic phosphorus compound is added and, when the aftertreatment is complete, is optionally washed and dried. If desired, the base particle is hydrothermally treated in advance and optionally aftertreated, before the reaction with the organic phosphorus compound is carried out.

The optional washing steps are advantageous if salt freight formed has to be removed. Whether and to what extent washing steps of this type have to be carried out is within the expert knowledge of the person skilled in the art.

A process for the production of the titanium dioxide particles according to the invention is, for example, characterised in that a stirrable dispersion of a titanium dioxide base particle is heated, the organic phosphorus compound is added and, when the aftertreatment is complete, is optionally washed and dried. The titanium dioxide base particle is optionally hydrothermally treated in advance and aftertreated with silicon hydroxide or oxide/dioxide, before the reaction with the organic phosphorus compound is carried out.

A preferred process for the production of preferred titanium dioxide particles in accordance with the invention is characterised in that
a) titanium dioxide particles, i.e. so-called titanium dioxide base particles, are hydrothermally treated,
b) a silicon dioxide coating is subsequently applied in such a way that the $SiO_2$ content in the coating corresponds to the values described above, particularly preferably corresponds to the values between 25 to 45 percent by weight, based on the $TiO_2$ content of the particles to be coated,
c) the stirrable dispersion from b) is heated, the organic phosphorus compound is added, optionally washed, and
d)) the suspension is dried.

The silicon dioxide coating in step b) can preferably be carried out as a sol-gel process, where a water-glass solution is particularly preferably added to a suspension of the titanium dioxide.

In an advantageous variant, the sol-gel process is carried out at a pH which is kept constant. The pH which is kept constant can be in a range from pH 2 to pH 11, where the pH is preferably in the range from pH=5 to pH=8, particularly preferably in the range from pH=6 to pH=7.

A further advantageous variant is the addition of all of the water-glass necessary for the aftertreatment at a pH=7 to pH=11 without the pH being kept constant. The pH is subsequently reduced to a value of pH=5 to pH=8, preferably to pH=6 to pH=7.

It is furthermore preferred for step b) to be carried out at elevated temperature, preferably at a temperature in the range from 50° C. to 110° C.

In all said variants of the process indicated, a ripening time when the coating is complete is advantageous. The ripening time should be between 1 h and 8 h, preferably 2 h to 4 h, and should be carried out at a temperature of 50° C. to 110° C.

The suspension obtained from c) can be used directly for the preparation of compositions comprising the titanium dioxide particles according to the invention. However, the suspension may also be dried.

It may furthermore be advantageous with respect to later processing if the product is subsequently ground. The conventional grinding techniques which can be used for nanoparticles can be employed here.

The nanoparticulate titanium dioxide according to the invention likewise has the advantageous properties of the comparative products from the prior art with respect to:
  UV absorption, in particular broad-band or UV-B absorption,
  transparency in visible light (VIS),
  good, in particular increased photostability,
  reduced or prevented photoactivity,
  silica surface which can optionally easily be hydrophobically modified using known techniques,
  easy dispersibility in aqueous and oily phases,
  in combination with dibenzoylmethane derivatives, in particular:
    reduced discoloration of the formulation and/or
    reducing discoloration of the formulation during storage and/or
    no or reduced crystallisation-out of complexes of the dibenzoylmethane derivatives and/or
    increased storage stability of the dibenzoylmethane derivatives and/or
    improved light-protection action, in particular after storage,
  in combination with reactive unstable constituents, for example benzophenone derivatives or ascorbic acid derivatives, in particular 2-hydroxy-4-methoxybenzophenone or ascorbyl palmitate, stabilisation of the benzophenone derivatives is observed.

The metal oxide particles and/or metal hydroxide particles according to Claim 1 according to the invention, in particular the nanoparticulate titanium dioxide according to the invention, exhibit/exhibits, in combination with dihydroxyacetone, significantly reduced degradation of the DHA after storage compared with conventional, previously known titanium dioxide UV protection agents, i.e. significant destabilisation of the self-tanning agent which is reduced compared with the prior art is observed. The titanium dioxide according to the invention is therefore referred to for the purposes of this invention as DHA-compatible. It has furthermore been found that, in combination with DHA, no or only minimal discoloration of the composition occurs after preparation and after storage for 3 months at 40° C. in the dark.

It has been found here, in particular, that, for simultaneous achievement of the above-mentioned advantages, it may be advantageous for the nanoparticulate titanium dioxide to be doped with iron.

Further preferred combinations of embodiments are disclosed in the claims.

Owing to the above-mentioned advantages, the present invention furthermore relates to a composition comprising the particles according to the invention, in particular the titanium dioxide particles according to the invention, as described above.

For the purposes of the present invention, the term agent or formulation is also used synonymously alongside the term composition.

All compounds or components which can be used in the compositions are either known and commercially available or can be synthesised by known processes.

The compositions in one variant of the invention are aqueous or oily dispersions. Preferred oils are, for example, natural oils, such as sunflower oil; or the oils known for use in cosmetics, such as isononyl isononanoate; isopropyl palmitate, propyl heptyl caprylate; dicaprylyl carbonate, butylene glycol dicaprylate/dicaprate, isopropyl lauroyl sarcosinate, C12-15 alkyl benzoate (for example Tegosoft TN from Evonik), capric/caprylic triglyceride, cyclopentasiloxanes or cyclohexasiloxanes.

The compositions in one variant of the invention are preferably compositions which can be applied topically, for example cosmetic or dermatological formulations. The compositions in this case comprise a cosmetically or dermatologically suitable carrier and, depending on the desired property profile, optionally further suitable ingredients.

Can be applied topically in the sense of the invention means that the composition is used externally and locally, i.e. that the composition must be suitable for application, for example, to the skin.

Further preferred compositions are selected from the group fibres, textiles, including coatings thereof, paints, coating systems, films and packaging for the protection of foods, plants or industrial products.

The nanoparticulate titanium dioxide according to the invention, as described above, can be used for incorporation into paints, coating systems, films, packaging, fibres, textiles and mouldings made from rubber or silicone rubber, such as tyres or insulators.

Particularly preferred compositions are the aqueous or oily dispersion and compositions which can be applied topically, in particular cosmetic compositions.

Besides the advantages already mentioned above, the use of the particles according to the invention in compositions which are emulsions may, in particular, also contribute to stabilisation of the emulsion. This can generally reduce the use of emulsifiers or in an individual case (Pickering emulsion), even make the use of emulsifiers totally superfluous. Preference is therefore also given in accordance with the invention to emulsifier-free emulsions which comprise the nanoparticulate titanium dioxide according to the invention.

The particles according to the invention may be present in the compositions according to the invention in proportions which are generally in the range from 0.1% by weight to 50% by weight and preferably in proportions which are in the range from 0.5% by weight to 20% by weight, where these proportions are based on the total weight of the composition.

Preferred compositions, in particular cosmetic compositions, comprise dihydroxyacetone or a dihydroxyacetone derivative, very particularly preferably dihydroxyacetone.

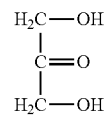

1,3-Dihydroxyacetone
(DHA)

The concentration of DHA in the composition is in the range from 1 to 12 percent by weight, preferably 1.5 percent by weight to 7.5 percent by weight, particularly preferably 2% by weight to 5% by weight, based on the composition.

These formulations are characterised in that the degradation of the DHA after storage for 3 months at 40° C. in the dark at different use ratios of the particle according to the invention, in particular of the titanium dioxide particle according to the invention, to DHA in percent by weight is not greater than a maximum of 20%, preferably not greater than 10%, relative to the DHA degradation in the same formulation without addition of metal oxide particles and/or metal hydroxide particles, in particular of titanium dioxide particles. In this respect, reference is made to the experimental part. The investigation results confirm that the DHA degradation after storage for 3 months at 40° C. in the dark for the titanium dioxide particles according to the invention is always less than the degradation in the case of titanium dioxide particles with other coatings without the coating according to the invention. Data which describe the absolute DHA degradation, based on the DHA use concentration, are also indicated therein.

In a further embodiment of the present invention, the composition according to the invention may comprise at least one further self-tanning agent besides dihydroxyacetone.

Advantageous self-tanning agents which can be employed, inter alia, are:

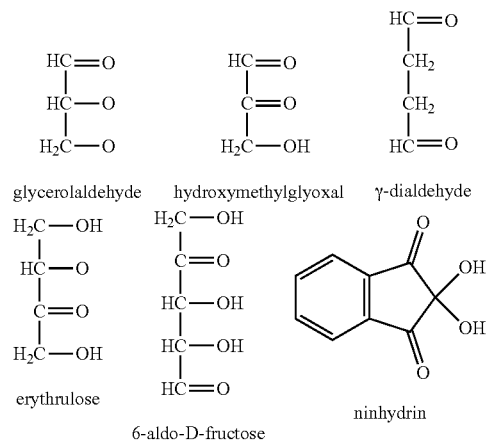

Furthermore, mention should be made of 5-hydroxy-1,4-naphtoquinone (juglone), which is extracted from the shells of fresh walnuts

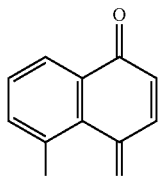

5-hydroxy-1,4-naphtoquinone (juglone)

and 2-hydroxy-1,4-naphtoquinone (lawsone), which occurs in henna leaves.

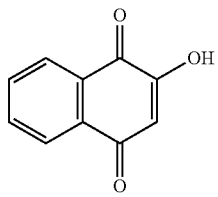

2-Hydroxy-1,4-naphtoquinone (lawsone)

The compositions according to the invention which comprise dihydroxyacetone tend towards malodours on application to the human skin, which are presumably caused by degradation products of the dihydroxyacetone itself or by products of side reactions and which are in some cases regarded as unpleasant by the users. It has been found that these malodours are avoided on use of formaldehyde scavengers and/or flavonoids. Neither can the occurrence of malodours be excluded on combined use with further self-tanning agents, as described above. The composition according to the invention may therefore preferably also comprise formaldehyde scavengers and optionally flavonoids in order to improve the odour.

The formaldehyde scavenger is preferably selected from the group alkali metal, alkaline-earth metal or ammonium bisulfite. Particular preference is given to a composition which comprises, in combination DHA Plus, a mixture of DHA, sodium bisulfite and magnesium stearate.

DHA Plus is a product mixture which comprises sodium bisulfite, synonymous with $Na_2S_2O_5$ or INCI: sodium disulfite, for the masking, elimination or neutralisation of the formaldehyde. The addition of sodium bisulfite to finished formulations results in a significant reduction or suppression of the unpleasant odour. DHA Plus is marketed by Merck, Darmstadt.

The flavonoid optionally present in the composition according to the invention additionally acts as stabiliser for the self-tanning agent or the self-tanning substances and/or reduces or prevents or improves storage-dependent malodours, which may also arise through additives or assistants present.

The flavonoid preferably contains one or more phenolic hydroxyl groups which are blocked by etherification or esterification. For example, hydroxyethyl-substituted flavonoids, such as, preferably, troxerutin, troxequercetin, troxeisoquercetin or troxeluteolin, and flavonoid sulfates or flavonoid phosphates, such as, preferably, rutin sulfates, have proven to be particularly suitable flavonoids here. For the purposes of the use according to the invention, particular preference is given to rutin sulfate and troxerutin. Very particular preference is given to the use of troxerutin.

The preferred flavonoids have a non-positively charged flavan skeleton. It is thought that these flavonoids complex metal ions, such as, for example, $Fe^{2+}/Cu^{2+}$, and thus prevent or reduce autooxidation processes in fragrances or compounds whose degradation results in malodours.

Particular preference is given to a composition which comprise DHA Rapid and/or sodium bisulfite. DHA Rapid is a product mixture comprising dihydroxyacetone and troxerutin, from Merck, Darmstadt.

Corresponding premixes and compositions which comprise formaldehyde scavengers and optionally flavonoids for improving the odour on the skin are described in the German patent application with the application file reference DE 10 2007 013 368.7, the contents of which in this respect expressly also belong to the disclosure content of the present application.

Furthermore, the particles according to the invention may also be employed with the following substances, alone or in combination with DHA, for intensification of tanning:
- Vegetan Premium (INCI Dihydroxyacetone/Melanin) from Soliance,
- MelanoBronze (INCI: *Vitex agnus castus* extract (and) acetyl tyrosine (and) glycerin (and) alcohol (and) water (aqua)) Mibelle AG Biochemistry.
- Instabronze® (INCI Dihydroxyaceton (DHA), N-acétyl tyrosine), Alban-Müller,
- substances which have a penetration-promoting action, such as, for example, empty liposomes, propylene glycol, isohexadecane (Arlamol HD; Croda), dimethyl isosorbide (Arlasolve DMI; CRODA), Trimethylpentanediol/Adipic Acid/Isononanoic Acid Copolymer (INCI name) or (Lexorez TC-8, Inolex).

The present invention furthermore relates to the use of the particles according to the invention, in particular of the nanoparticulate titanium dioxide according to the invention, for the stabilisation of dihydroxyacetone or dihydroxyacetone derivatives, in particular of dihydroxyacetone.

Furthermore, combinations of the particles according to the invention, in particular the titanium dioxide particles according to the invention, with further particulate UV filters, both as powder and also as dispersion or paste, of the following types are also possible.

Preference is given here both to those from the group of the titanium dioxides, such as, for example, coated titanium dioxide (for example Eusolex® T-2000, Eusolex®T-AQUA, Eusolex®T-AVO, Eusolex®T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments is greater than or equal to 200 nm, for example Hombitan® FG or Hombitan® FF-Pharma.

It may furthermore be possible for the compositions to comprise inorganic UV filters which have been aftertreated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

Further particulate UV filters which can be employed here are:
- untreated titanium dioxides, such as, for example, the products Microtitanium Dioxide MT 500 B from Tayca; titanium dioxide P25 from Degussa,
- aftertreated micronised titanium dioxides with aluminium oxide and silicon dioxide aftertreatment, such as, for example, the product "Microtitanium Dioxide MT 100 SA" from Tayca; or the product "Tioveil Fin" from Uniqema, aftertreated micronised titanium dioxides with aluminium oxide and/or aluminium stearate/laurate aftertreatment, such as, for example, Microtitanium Dioxide MT 100 T from Tayca, Eusolex T-2000 from Merck, aftertreated micronised titanium dioxides with iron oxide and/or iron stearate aftertreatment, such as, for example, the product "Microtitanium Dioxide MT 100 F" from Tayca, aftertreated micronised titanium dioxides with silicon dioxide, aluminium oxide and silicone aftertreatment, such as, for example, the product "Microtitanium Dioxide MT 100 SAS" from Tayca, aftertreated micronised titanium dioxides with sodium hexametaphosphates, such as, for example, the product "Microtitanium Dioxide MT 150 W" from Tayca.

The treated micronised titanium dioxides employed for the combination may also be aftertreated with:

octyltrimethoxysilanes; such as, for example, the product Tego Sun T 805 from Degussa, silicon dioxide; such as, for example, the product Parsol T-X from DSM, aluminium oxide and stearic acid; such as, for example, the product UV-Titan M160 from Sachtleben, aluminium and glycerin; such as, for example, the product UV-Titan from Sachtleben, aluminium and silicone oils, such as, for example, the product UV-Titan M262 from Sachtleben, sodium hexametaphosphate and polyvinylpyrrolidone, polydimethylsiloxanes, such as, for example, the product 70250 Cardre UF TiO2SI3 from Cardre, polydimethylhydrogenosiloxanes, such as, for example, the product Microtitanium Dioxide USP Grade Hydrophobic from Color Techniques, polymers, such as, for example, polyvinylpyrrolidone (PVP) or polyethylene (PE).

Combination with the following products may furthermore also be advantageous:

untreated zinc oxides, such as, for example, the product Z-Cote from BASF (Sunsmart), Nanox from Elementis aftertreated zinc oxides, such as, for example, the following products:

"Zinc Oxide CS-5" from Toshibi (ZnO aftertreated with poly-methylhydrogenosiloxanes)

Nanogard Zinc Oxide FN from Nanophase Technologies

"SPD-Z1" from Shin-Etsu (ZnO aftertreated with a silicone-grafted acrylic polymer, dispersed in cyclodimethylsiloxanes)

"Escalol Z100" from ISP (aluminium oxide-aftertreated ZnO dispersed in an ethylhexyl methoxycinnamate/PVP-hexadecene/methicone copolymer mixture)

"Fuji ZNO-SMS-10" from Fuji Pigment (ZnO aftertreated with silicon dioxide and polymethylsilsesquioxane)

untreated cerium oxide micropigment, for example with the name "Colloidal Cerium Oxide" from Rhone Poulenc untreated and/or aftertreated iron oxides with the name Nanogar from Arnaud.

For example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide, zinc oxide mixtures, such as, for example, the product UV-Titan M262 from Sachtleben, in combination with the UV protection agent according to the invention.

These inorganic UV filters are generally incorporated into cosmetic compositions in an amount of 0.1 percent by weight to 25 percent by weight, preferably 2% by weight-10% by weight. In particular, it may be preferred here for a nanoparticulate titanium dioxide according to the invention to be present in one phase in emulsions and a further inorganic UV filter to be present in the other phase.

Preferred compositions, in particular having light-protection properties, comprise at least one further UV filter, in particular a dibenzoylmethane derivative. The dibenzoylmethane derivatives used for the purposes of the present invention are products which are already well known per se and are described, in particular, in the above-mentioned specifications FR-A-2 326 405, FR-A-2 440 933 and EP-A-0 114 607.

The dibenzoylmethane derivatives which can be used in accordance with the invention may be selected, in particular, from the dibenzoylmethane derivatives of the following formula:

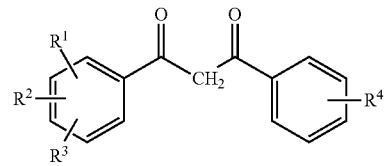

in which $R^1$, $R^2$, $R^3$ and $R^4$, which are identical or different from one another, denote hydrogen, a straight-chain or branched $C_{1-8}$-alkyl group or a straight-chain or branched $C_{1-8}$-alkoxy group. It is of course possible to use one dibenzoylmethane derivative or a plurality of dibenzoylmethane derivatives in accordance with the present invention. Of the dibenzoylmethane derivatives to which the present invention more specifically relates, mention may be made, in particular, of:

2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-methoxy-tert-butyldibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane, where this list is not restrictive.

Of the above-mentioned dibenzoylmethane derivatives, preference is given in accordance with the invention, in particular, to 4,4'-methoxy-tert-butyldibenzoylmethane and in particular 4,4'-methoxy-tert-butyldibenzoylmethane, which is commercially available under the trade name Eusolex® 9020 from Merck, where this filter conforms to the following structural formula:

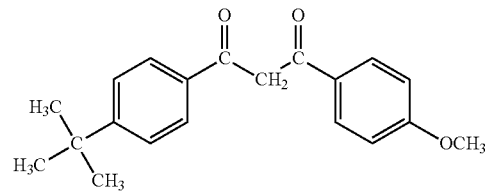 [SMILES: COc1ccc(C(=O)CC(=O)c2ccc(C(C)(C)C)cc2)cc1]

A further preferred dibenzoylmethane derivative is 4-isopropyldibenzoylmethane.

Further preferred compositions comprising further organic UV filters comprise at least one benzophenone or benzophenone derivative, such as, particularly preferably, 2-hydroxy-4-methoxybenzophenone (for example Eusolex® 4360) or 2-hydroxy-4-methoxybenzophenone-5-sulfonic acid and its sodium salt (for example Uvinul® MS-40).

The dibenzoylmethane derivative(s) or the benzophenone derivative(s) may be present in the compositions according to the invention in proportions which are generally in the range from 0.1% by weight to 10% by weight (percent by weight) and preferably in proportions which are in the range from 0.3% by weight to 5% by weight, where these proportions are based on the total weight of the composition.

The compositions according to the invention may of course comprise one or more additional hydrophilic or lipophilic sun-protection filter(s) which is (are) effective in the UV-A region and/or UV-B region and/or IR and/or VIS region (absorbers). These additional filters can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO 93/04665. Further examples of organic filters are indicated in the patent application EP-A 0 487 404. The said UV filters are usually named below in accordance with INCI nomenclature.

Particular mention should be made here of:

para-aminobenzoic acid and derivatives thereof: PABA, Ethyl PABA, Ethyl dihydroxypropyl PABA, Ethylhexyl dimethyl PABA, for example marketed under the name "Escalol 507" by ISP, Glyceryl PABA, PEG-25 PABA, for example marketed under the name "Uvinul P25" by BASF.

Salicylates: homosalate marketed under the name "Eusolex HMS" by Merck; ethylhexyl salicylate, for example marketed under the name "Neo Heliopan OS" by Haarmann and Reimer, dipropylene glycol salicylate, for example marketed under the name "Dipsal" by Scher, TEA salicylate, for example marketed under the name "Neo Heliopan TS" by Haarmann and Reimer.

β,β-Diphenylacrylate derivatives: octocrylene, for example marketed under the name "Eusolex OCR" by Merck, "Uvinul N539" by BASF, etocrylene, for example marketed under the name "Uvinul N35" by BASF.

Benzophenone derivatives: benzophenone-1, for example marketed under the name "Uvinul 400"; benzophenone-2, for example marketed under the name "Uvinul D50"; benzophenone-3 or oxybenzone, for example marketed under the name "Uvinul M40"; benzophenone-4, for example marketed under the name "Uvinul MS40"; benzophenone-9, for example marketed under the name "Uvinul DS-49" by BASF, benzophenone-5, benzophenone-6, for example marketed under the name "Helisorb 11" by Norquay, benzophenone-8, for example marketed under the name "Spectra-Sorb UV-24" by American Cyanamid, benzophenone-12 n-hexyl 2-(4-diethylamino-2-hydroxybenzoyl)benzoate.

Benzylidenecamphor derivatives: 3-benzylidenecamphor, for example marketed under the name "Mexoryl SD" by Chimex, 4-methylbenzylidene-camphor, for example marketed under the name "Eusolex 6300" by Merck, benzylidenecamphorsulfonic acid, for example marketed under the name "Mexoryl SL" by Chimex, camphor benzalkonium methosulfate, for example marketed under the name "Mexoryl SO" by Chimex, terephthalylidene-dicamphorsulfonic acid, for example marketed under the name "Mexoryl SX" by Chimex, polyacrylamidomethylbenzylidenecamphor marketed under the name "Mexoryl SW" by Chimex.

Phenylbenzimidazole derivatives: phenylbenzimidazolesulfonic acid, for example marketed under the name "Eusolex 232" by Merck, disodium phenyl dibenzimidazole tetrasulfonate, for example marketed under the name "Neo Heliopan AP" by Haarmann and Reimer.

Phenylbenzotriazole derivatives: drometrizole trisiloxane, for example marketed under the name "Silatrizole" by Rhodia Chimie, methylenebis(benzotriazolyl)tetramethylbutylphenol in solid form, for example marketed under the name "MIXXIM BB/100" by Fairmount Chemical, or in micronised form as an aqueous dispersion, for example marketed under the name "Tinosorb M" by Ciba Specialty Chemicals.

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl-4'-aminobenzalmalonate)-s-triazine.

Anthraniline derivatives: menthyl anthranilate, for example marketed under the name "Neo Heliopan MA" by Haarmann and Reimer.

Imidazole derivatives: ethylhexyldimethoxybenzylidenedioxoimidazoline propionate.

Benzalmalonate derivatives: polyorganosiloxanes containing functional benzalmalonate groups, such as, for example, polysilicone-15, for example marketed under the name "Parsol SLX" by Hoffmann LaRoche.

4,4-Diarylbutadiene derivatives: 1,1-dicarboxy(2,2'-dimethylpropyl)-4,4-diphenylbutadiene.

Benzoxazole derivatives: 2,4-bis[5-(1-dimethylpropyl)benzoxazol-2-yl(4-phenyl)imino]-6-(2-ethylhexyl)imino-1,3,5-triazine, for example marketed under the name Uvasorb K2A by Sigma 3V, and mixtures comprising this.

Piperazine derivatives, such as, for example, the compound

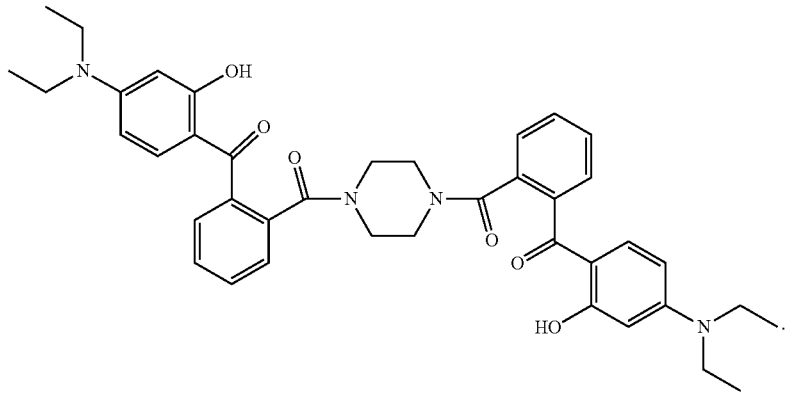 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

The compounds listed should only be regarded as examples. It is of course also possible to use other UV filters. In particular, organic particulate UV filters, as described, for example, in the patent application WO 99/66896, can advantageously also be combined with the particulate titanium dioxide particles according to the invention.

The organic UV-protecting substances which are suitable for combination with the UV protection agent according to the invention can preferably be selected from the following list: Ethylhexyl salicylate, Octocrylene, Butylmethoxydibenzoylmethane, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalyli-denedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-Bis[5-(1-dimethylpropyl)benzoxazol-2-yl(4-phenyl)imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Organic UV filters are generally incorporated into formulations in a total amount of 0.01 percent by weight to 20 percent by weight, preferably 0.5% by weight to 20% by weight.

Preferred compositions may also comprise compounds of the formula I

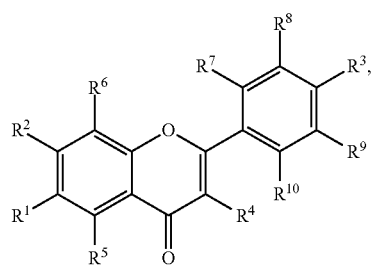

I where $R^1$ and $R^2$ are selected from
H
and $OR^{11}$, where $OR^{11}$, independently of one another, stands for
OH
straight-chain or branched $C_1$- to $C_{20}$-alkoxy groups,
straight-chain or branched $C_3$- to $C_{20}$-alkenyloxy groups,
straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or
$C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or
mono- and/or oligoglycosyl radicals,
with the proviso that at least one radical from $R^1$ and $R^2$ stands for $OR^{11}$, and $R^3$ stands for a radical $OR^{11}$ and $R^4$ to $R^7$ and $R^{19}$ may be identical or different and, independently of one another, stand for
H
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3, and
$R^8$ and $R^9$ may be identical or different and, independently of one another, stand for
H
$OR^{11}$
straight-chain or branched $C_1$- to $C_{20}$-alkyl groups,
straight-chain or branched $C_3$- to $C_{20}$-alkenyl groups,
straight-chain or branched $C_1$- to $O_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3.

Advantages of the compositions here are, in particular, the UV light-filtering action and the good skin tolerance. In addition, the compounds of the formula I described here are colourless or only weakly coloured and thus, in contrast to many known naturally occurring flavonoids, do not result in discoloration of the compositions.

The flavonoids of the above-mentioned formula to be employed in accordance with the invention include broadband UV filters, other likewise preferred compounds of the above-mentioned formula exhibit an absorption maximum in the boundary region between UV-B and UV-A radiation. As UV-A-II filters, they therefore advantageously supplement the absorption spectrum of commercially available UV-B and UV-A-I filters. Preferred compositions having light-protection properties according to the invention comprise at least one compound of the above-mentioned formula, where $R^3$ stands for
OH or
straight-chain or branched $C_1$- to $C_{20}$-alkoxy groups, preferably methoxy, ethoxy or ethylhexyloxy, or
mono- and/or oligoglycosyl radicals, preferably glucosyl radicals, and
$R^1$ and/or $R^2$ preferably stand for
OH or
straight-chain or branched $C_1$- to $C_{20}$-alkoxy groups, preferably methoxy, ethoxy or ethylhexyloxy, or
mono- and/or oligoglycosyl radicals, preferably glucosyl radicals.

These preferred compounds are distinguished by particularly strong UV absorption.

In addition, preferred compounds of this type have advantages on incorporation into the compositions:
mono- and/or oligoglycosyl radicals improve the water solubility of the compounds to be employed in accordance with the invention;
straight-chain or branched $C_1$- to $C_{20}$-alkoxy groups, in particular the long-chain alkoxy functions, such as ethylhexyloxy groups, increase the oil solubility of the compounds;

i.e. the hydrophilicity or lipophilicity of the compounds of the formula I can be controlled via a suitable choice of the substituents. Preferred mono- or oligosaccharide radicals here are hexosyl radicals, in particular rhamnosyl radicals and glucosyl radicals. However, other hexosyl radicals, for example allosyl, altrosyl, galactosyl, gulosyl, idosyl, mannosyl and talosyl, may also, if desired, advantageously be used. It may also be advantageous to use pentosyl radicals. The glycosyl radicals can be bonded to the parent substance α- or β-glycosidically. A preferred disaccharide is, for example, 6-O(6-deoxy-α-L-mannopyranosyl)-β-D-glucopyranoside.

It has been found that the intensity of the UV absorption is particularly high if $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy.

Compositions having light-protection properties comprising at least one compound of the above-mentioned formula which is characterised in that $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy are therefore particularly preferred in accordance with the invention. It is particularly preferred here if $R^8$ and $R^9$ stand for H.

The compounds of the above-mentioned formula are typically employed in amounts of 0.01% by weight to 20% by weight, preferably in amounts of 0.5% by weight to 10% by weight and particularly preferably in amounts of 1% by weight to 8% by weight. The person skilled in the art is presented with absolutely no difficulties at all in correspondingly selecting the amounts depending on the intended light protection factor of the composition.

Combination of the titanium dixide particles according to the invention with further UV filters enables the protective action against harmful effects of UV radiation to be optimised. Optimised compositions may comprise, for example, the combination of the organic UV filters 4'-methoxy-6-hydroxyflavone with 1-(4-tert-butylphenyl)-3-(4-methoxyphenyl)propane-1,3-dione and 3-(4'-methylbenzylidene)-dl-camphor.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables preparation problems caused by the interaction of individual composition constituents with one another, such as crystallisation processes, precipitation and agglomeration, to be avoided since the interaction is suppressed.

It may therefore be preferred in accordance with the invention for one or more of the compounds of the formula I or (which formula I) the above-mentioned UV filters to be in encapsulated form. It is advantageous here for the capsules to be so small that they cannot be observed with the naked eye. In order to achieve the above-mentioned effects, it is furthermore necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed in accordance with the invention have walls which can be obtained by a sol-gel process, as described in the applications WO 00/09652, WO 00/72806 and WO 00/71084. Preference is in turn given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

Furthermore, the compositions according to the invention may also comprise dyes and coloured pigments. The dyes and coloured pigments can be selected from the corresponding positive list of the German Cosmetics Regulation or the EC list of cosmetic colorants. In most cases, they are identical with the dyes approved for foods. Advantageous coloured pigments are, for example, titanium dioxide, mica, iron oxides (for example $Fe_2O_3$, $Fe_3O_4$, FeO(OH)) and/or tin oxide. Advantageous dyes are, for example, carmine, Berlin Blue, Chromium Oxide Green, Ultramarine Blue and/or Manganese Violet. It is particularly advantageous to select the dyes and/or coloured pigments from the following list. The Colour Index numbers (CINs) are taken from the Rowe Colour Index, 3rd Edition, Society of Dyers and Colourists, Bradford, England, 1971.

It may furthermore be favourable to select one or more substances from the following group as dye:
2,4-dihydroxyazobenzene, 1-(2'-chloro-4'-nitro-1'phenylazo)-2-hydroxynaphthalene, Ceres Red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminium salt of 1-(4-sulfo-1-phenylazo)-2-naphthol-6-sulfonic acid, aluminium salt of 1-(4-sulfo-1-naphthylazo)-2-naphthol-3,6-disulfonic acid, 1-(4-sulfo-1-naphthylazo)-2-naphthol-6,8-disulfonic acid, aluminium salt of 4-(4-sulfo-1-phenylazo)-2-(4-sulfophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalonedisulfonic acid, aluminium salt indigodisulfonic acid, red and black iron oxide (CIN:

77 491 (red) and 77 499 (black)), iron oxide hydrate (CIN: 77492), manganese ammonium diphosphate and titan dioxide.

Furthermore suitable are oil-soluble natural dyes, such as, for example, paprika extract, β-carotene or cochenille.

Furthermore advantageous for the purposes of the present invention are gel creams having a content of pearlescent pigments or interference pigments, in particular pigments whose compatibility with Preference is given in particular, to the pearlescent pigments or interference pigments die which are based on a flake-form substrate and are coated with titanium dioxide and/or iron oxide ($Fe_2O_3$) and optionally have a final $SiO_2$ layer.

Particularly preferred pigments are, for example, the pigments available from Merck under the trade names Timiron®, Colorona®, Dichrona® or Sirona®.

The total amount of the dyes and colouring pigments is advantageously selected from the range from, for example, 0.1% by weight to 30% by weight, preferably from 0.5% by weight to 15% by weight, in particular from 1.0% by weight to 10% by weight, in each case based on the total weight of the compositions.

The protective action against oxidative stress or against the effect of free radicals can be further improved if the compositions comprise one or more antioxidants.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, pentasodium ethylenediaminetetramethylenephosphonate (INCI: Pentasodium ethylenediamine tetramethylene phosphonate), unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the formulae A or B

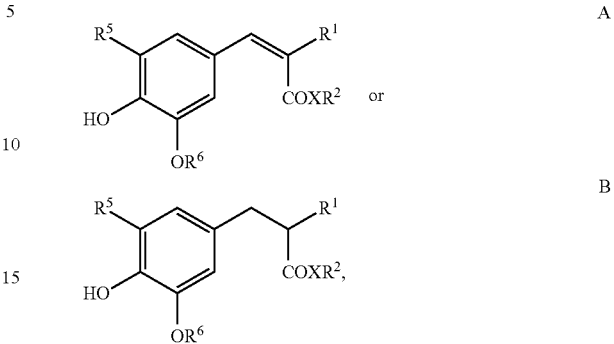

in which
$R^1$ can be selected from the group —$C(O)CH_3$, —$CO_2R^3$, —$C(O)NH_2$ and —$C(O)N(R^4)_2$,
X denotes O or NH,
$R^2$ denotes linear or branched alkyl having 1 to 30 C atoms,
$R^3$ denotes linear or branched alkyl having 1 to 20 C atoms,
$R^4$, in each case independently of one another, denotes H or linear or branched alkyl having 1 to 8 C atoms,
$R^5$ denotes H or linear or branched alkyl having 1 to 8 C atoms or linear or branched alkoxy having 1 to 8 C atoms and
$R^6$ denotes or linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably 2-(4-hydroxy-3,5-dimethoxybenzylidene)malonic acid bis(2-ethylhexyl) ester (e.g. Oxynex® ST Liquid) and/or 2-(4-hydroxy-3,5-dimethoxybenzy)malonic acid bis(2-ethylhexyl) ester (e.g. RonaCare® AP). The said compounds of the formula A or B are also advantageous photostabilisers for organic UV filters, but also other photosensitive compounds, such as, for example, perfume or dyes.

Mixtures of antioxidants are likewise suitable for use in the cosmetic compositions according to the invention. Known and commercial mixtures are, for example, mixtures comprising, as active compounds, lecithin, L-(+)ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin A palmitate, vitamin C, DL-α-tocopherol, tocopherol E acetate, nicotinic acid, pantothenic acid and biotin.

The compositions according to the invention may in addition comprise further conventional skin-protecting or skin-care active compounds. These can in principle be any active compounds known to the person skilled in the art.

Particularly preferred active compounds are pyrimidinecarboxylic acids and/or aryl oximes.

Preference is given here to the use of a pyrimidinecarboxylic acid of the following formula II

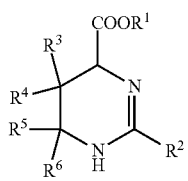

in which $R^1$ is a radical H or C1-8-alkyl, $R^2$ is a radical H or C1-4-alkyl, and $R^3$, $R^4$, $R^5$ and $R^6$ are each, independently of one another, a radical from the group H, OH, $NH_2$ and $C_{1-4}$-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which comprise aryl oximes, preferably 2-hydroxy-5-methyllaurophenone oxime, exhibit surprising antiinflammatory suitability. The compositions here preferably comprise 0.01% by weight to 10% by weight of the aryl oxime, it being particularly preferred for the composition to comprise 0.05% by weight to 5% by weight of aryl oxime.

All compounds or components described here that can be used in the compositions are either known and commercially available or can be synthesised by known processes.

The compositions according to the invention can be prepared by processes which are well known to the person skilled in the art, in particular by the processes which serve for the preparation of oil-in-water emulsions or water-in-oil emulsions.

The present invention furthermore relates to a process for the preparation of a composition which is characterised in that the particles according to the invention, as described above, is mixed with a cosmetically or dermatologically suitable vehicle and optionally further ingredients, as described above.

These compositions can be, in particular, in the form of simple or complex emulsions (O/W, W/O, O/W/O or W/O/W), such as creams, milks, gels or gel creams, powders and solid sticks, and they may, if desired, be formulated as aerosols and be in the form of foams or sprays. These compositions are preferably in the form of an O/W emulsion.

The cosmetic compositions according to the invention can be used as composition for protection of the human epidermis or of the hair against UV radiation, for skin care, as sunscreen, self-tanning agent or make-up products.

It should be pointed out that in the formulations according to the invention which comprise a vehicle of the oil-in-water emulsion type, the aqueous phase (which comprises, in particular, the hydrophilic filters) generally makes up 50% by weight to 95% by weight and preferably 70% by weight to 90% by weight, based on the formulation as a whole, the oil phase (which comprises, in particular, the lipophilic filters) makes up 5% by weight to 50% by weight and preferably 10% by weight to 30% by weight, based on the formulation as a whole, and the (co)emulsifier or (co)emulsifiers make(s) up 0.5% by weight to 20% by weight and preferably 2% by weight to 10% by weight, based on the formulation as a whole.

Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower products. Any desired customary vehicles, assistants and, if desired, further active compounds may be added to the composition.

Preferred assistants originate from the group of preservatives, antioxidants, stabilisers, solubilisers, vitamins, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerin fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerin, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerin fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerin, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acids and saturated and/or unsaturated, branched and/or unbranched alcohols having a chain length of 3 to 30 C atoms. Ester oils of this type can then advantageously be selected from the group of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of branched and unbranched hydrocarbons and hydrocarbon waxes, silicone oils, dialkyl ethers, or the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may advantageously be selected, for example, from the group of synthetic, semi-synthetic and natural oils, for example olive oil, sunflower oil, soya oil, peanut oil, rapeseed oil, almond oil, palm oil, coconut oil, palm kernel oil and the like.

Any desired blends of oil and wax components of this type may also advantageously be employed for the purposes of the present invention. It may also be advantageous to employ waxes, for example cetyl palmitate, as the only lipid component of the oil phase.

The oil phase is advantageously selected from the group of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride, dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane, poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerin, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerin, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

In a preferred embodiment, the compositions according to the invention comprise hydrophilic surfactants.

The hydrophilic surfactants are preferably selected from the group consisting of the alkylglucosides, acyl lactylates, betaines and coconut amphoacetates.

Alkylglucosides which are particularly advantageously used in accordance with the invention are selected from the group of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS 10 (Seppic).

The acyllactylates are themselves advantageously selected from the group of the substances which are distinguished by the structural formula

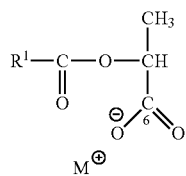

where $R^1$ denotes a branched or unbranched alkyl radical having 1 to 30 carbon atoms, and $M^+$ is selected from the group consisting of the alkali metal ions and the group consisting of ammonium ions which are substituted by one or more alkyl and/or by one or more hydroxyalkyl radicals, or corresponds to half an equivalent of an alkaline earth metal ion.

For example, sodium isostearyl lactylate, for example the product Path-ionic® ISL from the American Ingredients Company, is advantageous.

For the group of the betaines, capramidopropylbetaine, for example the product Tego® Betain 810 from Th. Goldschmidt AG, is, for example, advantageous.

A coconut amphoacetate which is advantageously selected in accordance with the invention is, for example, sodium coconut amphoacetate, as available under the name Miranol® Ultra C32 from Miranol Chemical Corp.

The compositions according to the invention are advantageously characterised in that the hydrophilic surfactant or the hydrophilic surfactants is or are present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

An emulsifier that has proven to be particularly preferred in accordance with the invention for O/W emulsions is the commercial product Ceralution C from Sasol.

Co-emulsifiers which are advantageously selected in accordance with the invention are, for example, O/W emulsifiers, principally from the group consisting of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or if isoalkyl derivatives are present, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following:

polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:

fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/0 emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Compositions which are preferred in accordance with the invention are particularly suitable for protecting human skin against UV-induced ageing processes and against oxidative stress, i.e. against damage caused by free radicals, as are generated, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants that are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerin and sorbitol.

A preferred embodiment of the invention is an emulsion in the form of a protective cream or milk which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerin, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerin, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or setting a water wave, in the form of a hair lacquer, permanent-waving composition, colorant or bleach for the hair. The composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The compositions, as described above, may comprise or include, essentially consist of or consist of the said necessary or optional constituents/ingredients.

The invention is explained in greater detail below with reference to examples.

EXAMPLES

Example of the Determination of $SiO_2$ or the Determination of the After-treatment Substance Comprising Si.

5 g of soda/borax mixture 7+1 are added to 0.1 g to 0.5 g of the sample (weighed to an accuracy of 0.0001), depending on the expected content of Si, in a small platinum crucible, and the mixture is digested for about 30 minutes. After cooling, the melt is leached out in 50 ml of cold dilute hydrochloric acid, the batch is transferred into a volumetric flask with a capacity of 250 ml, made up to the mark with bidistilled water and shaken carefully ($CO_2$).

The silicic acid is determined, depending on the content, either directly or after appropriate dilution (the maximum digestion agent concentration for the measurement on the ICP-OES is 2%). A chemicals blank set is obligatory.

The calibration is carried out with the aid of standard solutions whose matrix corresponds to the sample matrix.

The measurement is carried out on the instrument (ICP-OES) from Perkin Elmer, Optima 3300DV, using the instrument operating manual. The $SiO_2$ content is determined here on the entire particle, i.e. the values are below the indicated values for the $SiO_2$ content based on the $TiO_2$ content of the particles to be coated.

For the Si→$SiO_2$ calculation 2.139
$SiO_2$*1.220=simethicone
Reagents and Solutions Used:
Soda, anhydrous, p.a.
Borax, sodium tetraborate, p.a.
Hydrochloric acid, p.a. 1+1 diluted with bidistilled water.

Example of the Determination of the Content of Organic Phosphorus Compound by Determination of the Carbon Content.

The operation of the automatic CS analyser employed, for example Eltra CS580, is assumed to be known or is indicated in the corresponding operating manual.

0.1 g to 0.5 g of the sample (weighed to an accuracy of 0.0001) are weighed out into a carrier boat.

The sample is moved into the heating zone of the combustion tube, where it is burned at 1300° C. in a stream of oxygen. The carbon determination is carried out automatically by the analyser and is completed by the output of the carbon content.

Checking and calibration of the measuring instrument using company internal standard samples and British Chemical Standards (B.C.S.) reference standard.

In order to determine the content of organic phosphorus compound, the carbon content obtained is calculated via the carbon content of the organic phosphorus compound. Since the latter differs depending on the phosphorus compound employed, the calculation is indicated with reference to a fictitious example: the organic phosphorus compound employed as starting material comprises 67% of C.

In the determination of the carbon content of the aftertreated sample, a value of 6.7% of C was determined.

67% of C corresponds to 100% of organic phosphorus compound
6.7% of C corresponds to $$\frac{6.7 \times 100}{67} = 10\%$$

of organic phosphorus compound
The aftertreated sample thus comprises 10% of the organic phosphorus compound.

Example 1a

Preparation of Titanium Dioxide Starting Material xl of an aqueous suspension of metatitanic acid having a content of around 370 g of $TiO_2$/l are mixed with 0.9×l of water and ×l of 50% sodium hydroxide solution, heated to the boiling point with stirring and held at the temperature for 2 h. The sodium titanate formed in the process is washed and adjusted to a content of about 100-110 g of $TiO_2$/l using water. The titanate is heated to 60° C. It is then acidified to pH 2 using 30% HCl, subsequently stirred at the temperature and the pH for 45 min.

Contents of 45 g of HCl/l and 90 g of $TiO_2$/l are subsequently set using water and 30% hydrochloric acid, and the suspension is held at 85° C. with stirring for 6 h ("peptisation").

The peptised suspension is slowly neutralised to pH 5.5 using 50% NaOH.

Comparative Example 1b

Titanium Dioxide without Aftertreatment

The material obtained from Example 1a is filtered off and washed with water to a conductivity<100 μS/cm. The filter cake obtained comprises about 18% of product. The filter cake is dried and de-aggregated.

Example 1c

Hydrothermal Treatment (HT)

The material obtained from Example 1a is diluted to 50 g of $TiO_2$/l and subjected to a hydrothermal treatment in the pressure container at 180° C. for a period of 2 h.

Example 1d

Aftertreatment with 20% of $SiO_2$

An amount of the material obtained from Example 1a corresponding to ×g of $TiO_2$ is diluted to 50 g of $TiO_2$/l, and an amount of sodium water-glass solution (concentration: about 270 g of $SiO_2$/l) which corresponds to 0.2×g of $SiO_2$ is subsequently added at 80° C., and the pH, which rises in the process, is kept constant at pH 9.0 using dilute sulfuric acid.

After addition of all the water-glass solution, a pH of 6.5 is set using $H_2SO_4$, and the suspension is allowed to ripen at the temperature and the pH with stirring for 2 h. The suspension obtained comprises about 6 to 7% of product.

Example 1e

Aftertreatment with 35% of $SiO_2$ 5

An amount of the material obtained from Example 1a corresponding to xg of $TiO_2$ is diluted to 50 g of $TiO_2$/l, and an amount of sodium water-glass solution (concentration: about 270 g of $SiO_2$/l) which corresponds to 0.35×g of $SiO_2$ is subsequently added at 80° C., and the pH, which rises in the process, is kept constant at pH 9.0 using dilute sulfuric acid.

After addition of all the water-glass solution, a pH of 6.5 is set using $H_2SO_4$, and the suspension is allowed to mature at the temperature and the pH with stirring for 2 h. The suspension obtained comprises about 6 to 8% of product.

Example 1f

Aftertreatment with 20% of $SiO_2$ on HT-Treated Base Particle

An amount of sodium water-glass solution (concentration: about 270 g of $SiO_2$/l) which corresponds to 0.2×g of $SiO_2$ is added at 80° C. to an amount of the material obtained from Example 1c corresponding to xg of $TiO_2$, and the pH, which rises in the process, is kept constant at pH 9.0 using dilute sulfuric acid.

After addition of all the water-glass solution, a pH of 6.5 is set using $H_2SO_4$, and the suspension is allowed to mature at the temperature and the pH with stirring for 2 h. The suspension obtained comprises about 6 to 7% of product.

Example 1g

Aftertreatment with 35% of $SiO_2$ on HT-Treated Base Particle

An amount of sodium water-glass solution (concentration: about 270 g of $SiO_2$/l) which corresponds to 0.35×g of $SiO_2$ is added at 80° C. to an amount of the material obtained from Example 1c corresponding to xg of $TiO_2$, and the pH, which rises in the process, is kept constant at pH 9.0 using dilute sulfuric acid.

After addition of all the water-glass solution, a pH of 6.5 is set using $H_2SO_4$, and the suspension is allowed to mature at the temperature and the pH with stirring for 2 h. The suspension obtained comprises about 7 to 8% of product.

Comparative Example 2a

Titanium Dioxide Comprising 20% of $SiO_2$

The material obtained from Example 1d is filtered off and washed with water to a conductivity<100 µS/cm. The filter cake obtained comprises about 18% of product. The filter cake is dried and de-aggregated.

Comparative Example 2b

Titanium Dioxide Comprising 35% of $SiO_2$

The material obtained from Example 1e is filtered off and washed with water to a conductivity<100 µS/cm. The filter cake obtained comprises about 18% of product. The filter cake is dried and de-aggregated.

Comparative Example 3a

HT-Treated Titanium Dioxide Comprising 20% of $SiO_2$

The material obtained from Example 1f is filtered off and washed with water to a conductivity<100 µS/cm. The filter cake obtained comprises about 18% of product. The filter cake is dried and de-aggregated.

Comparative Example 3b

HT-Treated Titanium Dioxide Comprising 35% of $SiO_2$

The material obtained from Example 1 g is filtered off and washed with water to a conductivity<100 µS/cm. The filter cake obtained comprises about 18% of product. The filter cake is dried and de-aggregated.

Example 4a

Titanium Dioxide Comprising 35% of $SiO_2$ and 5% of Phosphoric Acid Monocetyl Ester The material obtained from Example 1e is filtered off and washed with water to a conductivity<100 µS/cm. The filter cake obtained comprises about 18% of solid. An amount of the filter cake corresponding to xg of solid is diluted with a little water and heated to 80° C. 0.05×g of Hostaphat CC100 (phosphoric acid monocetyl ester) from Clariant are added to the suspension with stirring, and the mixture is stirred at constant temperature for a further 10 minutes. The suspension is cooled with stirring, dried and de-aggregated.

Example 4b

Titanium Dioxide Comprising 35% of $SiO_2$ and 10% of Phosphoric Acid Monocetyl Ester The material obtained from Example 1e is filtered off and washed with water to a conductivity<100 µS/cm. The filter cake obtained comprises about 18% of solid. An amount of the filter cake corresponding to xg of solid is diluted with a little water and heated to 80° C. 0.1×g of Hostaphat CC100 (phosphoric acid monocetyl ester) from Clariant are added to the suspension with stirring, and the mixture is stirred at constant temperature for a further 10 minutes. The suspension is cooled with stirring, dried and de-aggregated.

Example 4c

Titanium Dioxide Comprising 35% of $SiO_2$ and 15% of Phosphoric Acid Monocetyl Ester An amount of the suspension from Example 1e corresponding to xg of solid (washed until salt-free) is heated to 80° C. 0.15×g of Hostaphat CC100 (phosphoric acid monocetyl ester) from Clariant are added to the suspension with stirring, and the mixture is stirred at constant temperature for a further 10 minutes. The suspension is cooled with stirring, filtered off and washed with water to a conductivity<100 µS/cm. The filter cake obtained is dried and de-aggregated.

Example 4d

Titanium Dioxide Comprising 35% of SiO$_2$ and 15% of Phosphoric Acid Mono- and Distearyl Ester Mixture The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.15×g of Hostaphat CS120 (phosphoric acid mono- and distearyl ester mixture) from Clariant are added to the suspension with stirring, and the mixture is stirred at constant temperature for a further 10 minutes. The suspension is cooled with stirring, dried and de-aggregated.

Example 4e

Titanium Dioxide Comprising 35% of SiO$_2$ and 15% of 1-hydroxyethane-1,1-diphosphonic acid The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.25×g of Cublen K60 (comprises about 60% of 1-hydroxyethane-1,1-diphosphonic acid) from Zschimmer & Schwarz Mohsdorf are added to the suspension with stirring, and the mixture is stirred at constant temperature for a further 30 minutes. The suspension is cooled with stirring, dried and de-aggregated.

Example 4f

Titanium Dioxide Comprising 35% of SiO$_2$ and 15% of 2-phosphonobutane-1,2,4-tricarboxylic acid The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.3×g of Cublen P50 (comprises about 50% of 2-phosphonobutane-1,2,4-tricarboxylic acid) from Zschimmer & Schwarz Mohsdorf are added to the suspension with stirring, and the mixture is stirred at constant temperature for a further 30 minutes. The suspension is cooled with stirring, dried and de-aggregated.

Example 4

Titanium Dioxide Comprising 35% of SiO$_2$ and 15% of Aminotrismethylenephosphonic Acid The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.3×g of Cublen AP5 (comprises about 50% of aminotrismethylenephosphonic acid) from Zschimmer & Schwarz Mohsdorf are added to the suspension with stirring, and the mixture is stirred at constant temperature for a further 30 minutes. The suspension is cooled with stirring, dried and de-aggregated.

Example 4h

Titanium Dioxide Comprising 35% of SiO$_2$ and 15% of Laurylphosphonic Acid The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.15×g of laurylphosphonic acid from Rhodia are added to the suspension with stirring, and the mixture is stirred at constant temperature for a further 30 minutes. The suspension is cooled with stirring, dried and de-aggregated.

Example 4i

Titanium Dioxide Comprising 35% of SiO$_2$ and 15% of Octylphosphonic Acid

The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.15×g of octylphosphonic acid from Rhodia are added to the suspension with stirring, and the mixture is stirred at constant temperature for a further 30 minutes. The suspension is cooled with stirring, dried and de-aggregated.

Example 4k

Titanium Dioxide Comprising 35% of SiO$_2$ and 5% of 1-hydroxydodecane-1,1-diphosphonic acid The material obtained from Example 1e is filtered off and washed with water to a conductivity<100 μS/cm. The filter cake obtained comprises about 18% of solid. An amount of the filter cake corresponding to xg of solid is diluted with a little water and heated to 80° C. 0.067×g of Tensan AO concentrate (comprises about 75% of 1-hydroxydodecane-1,1-diphosphonic acid) from Polygon Chemie are added to the suspension with stirring, and the mixture is stirred at constant temperature for a further 30 minutes. The suspension is cooled with stirring, dried and de-aggregated.

Example 5a

HT Titanium Dioxide Comprising 20% of SiO$_2$ and 3% of Phosphoric Acid Monocetyl Ester The material obtained from Example 1f is filtered off and washed with water to a conductivity<100 μS/cm. An amount of the filter cake corresponding to xg of solid is diluted with a little water and heated to 80° C. 0.03×g of Hostaphat CC100 (phosphoric acid monocetyl ester) from Clariant are added to the suspension with stirring, and the mixture is stirred at constant temperature for a further 10 minutes. The suspension is cooled with stirring, dried and de-aggregated.

Example 5b

HT Titanium Dioxide Comprising 20% of SiO$_2$ and 6% of Phosphoric Acid Monocetyl Ester An amount of the suspension from Example 1f corresponding to xg of solid (washed until salt-free) is heated to 80° C.

0.06×g of Hostaphat CC100 (phosphoric acid monocetyl ester) from Clariant are added to the suspension with stirring, and the mixture is stirred at constant temperature for a further 45 minutes. The suspension is filtered off while hot and washed with water to a conductivity<100 μS/cm. The filter cake obtained is dried and de-aggregated.

Example 5c

HT Titanium Dioxide Comprising 20% of $SiO_2$ and 9% of Phosphoric Acid Monocetyl Ester The material obtained from Example 1f is filtered off and washed with water to a conductivity<100 μS/cm. An amount of the filter cake corresponding to ×g of solid is diluted with a little water and heated to 80° C. 0.09×g of Hostaphat CC100 (phosphoric acid monocetyl ester) from Clariant are added to the suspension with stirring, and the mixture is stirred at constant temperature for a further 10 minutes. The suspension is cooled with stirring, dried and de-aggregated.

Example 5d

HT Titanium Dioxide Comprising 35% of $SiO_2$ and 3% of Phosphoric Acid Monocetyl Ester The material obtained from Example 1g is filtered off and washed with water to a conductivity<100 μS/cm. An amount of the filter cake corresponding to ×g of solid is diluted with a little water and heated to 80° C. 0.03×g of Hostaphat CC100 (phosphoric acid monocetyl ester) from Clariant are added to the suspension with stirring, and the mixture is stirred at constant temperature for a further 10 minutes. The suspension is cooled with stirring, dried and de-aggregated.

Example 5e

HT Titanium Dioxide Comprising 35% of $SiO_2$ and 6% of Phosphoric Acid Monocetyl Ester An amount of the suspension from Example 1g corresponding to ×g of solid (washed until salt-free) is heated to 80° C. 0.06×g of Hostaphat CC100 (phosphoric acid monocetyl ester) from Clariant are added to the suspension with stirring, and the mixture is stirred at constant temperature for a further 30 minutes. The suspension is filtered off while hot and washed with water to a conductivity<100 μs/cm. The filter cake obtained is dried and de-aggregated.

Example 5f

HT Titanium Dioxide Comprising 35% of $SiO_2$ and 9% of Phosphoric Acid Monocetyl Ester The material obtained from Example 1g is filtered off and washed with water to a conductivity<100 μS/cm. An amount of the filter cake corresponding to ×g of solid is diluted with a little water and heated to 80° C. 0.09×g of Hostaphat CC100 (phosphoric acid monocetyl ester) from Clariant are added to the suspension with stirring, and the mixture is stirred at constant temperature for a further 10 minutes. The suspension is cooled with stirring, dried and de-aggregated.

Comparative Example 6a

Titanium Dioxide Comprising 20% of $SiO_2$ and 10% of Simethicone

The material obtained from Example 1f is filtered off and washed with water to a conductivity<100 μS/cm. An amount of the filter cake corresponding to ×g of solid is liquefied using a little water. 0.33×g of Sentry Simethicone Emulsion USP (comprises about 30% of simethicone) from OSi are added to the suspension with vigorous stirring, and the mixture is stirred for a further 30 minutes. The suspension is dried and de-aggregated.

Comparative Example 6b

HT Titanium Dioxide Comprising 20% of $SiO_2$ and 10% of Simethicone

The material obtained from Example 1f is filtered off and washed with water to a conductivity<100 μS/cm. An amount of the filter cake corresponding to ×g of solid is liquefied using a little water. 0.33×g of Sentry Simethicone Emulsion USP (comprises about 30% of simethicone) from OSi are added to the suspension with vigorous stirring, and the mixture is stirred for a further 30 minutes. The suspension is dried and de-aggregated.

Comparative Example 6c

HT Titanium Dioxide Comprising 35% of $SiO_2$ and 10% of Simethicone

The material obtained from Example 1d is filtered off and washed with water to a conductivity<100 μS/cm. An amount of the filter cake corresponding to ×g of solid is liquefied using a little water. 0.33×g of Sentry Simethicone Emulsion USP (comprises about 30% of simethicone) from OSi are added to the suspension with vigorous stirring, and the mixture is stirred for a further 30 minutes. The suspension is dried and de-aggregated.

Example 7a

Titanium dioxide comprising 12% of $Al_2O_3$ and 10% of Octylphosphonic Acid

An amount of sodium aluminate solution (concentration about 260 g of $Al_2O_3$/l) which corresponds to 0.12×g of $Al_2O_3$ is added at 80° C. to an amount of the material obtained from Example 1a corresponding to ×g of $TiO_2$, and the pH, which rises in the process, is kept constant at pH 7.0 using dilute sulfuric acid.

When all the aluminate solution has been added, a pH of 6.5 is set using $H_2SO_4$, and the suspension is allowed to mature at the temperature and the pH with stirring for 2 h. The suspension is filtered off and washed with water to a conductivity<100 μS/cm. An amount of the filter cake corresponding to y g of solid is liquefied using a little water. 0.1y g of octylphosphonic acid from Albright & Wilson are added to the suspension with vigorous stirring, and the mixture is stirred for a further 30 minutes. The suspension is dried and de-aggregated.

Comparative Example 7b

Titanium Dioxide Comprising 12% of $Al_2O_3$ and 10% of Stearic Acid

Commercial product: EUSOLEX T-S from Merck

Comparative Example 8a

Titanium Dioxide Comprising 10% of $SiO_2$ and 9% of Methicone

Commercial product: UV-Titan X195 from Kemira (now Sachtleben Chemie)

Comparative Example 8b

Titanium Dioxide Comprising 10% of $SiO_2$ and 9% of Methicone

Commercial product: UV-Titan M195 from Kemira (now Sachtleben Chemie)

Comparative Example 8d

Titanium Dioxide Comprising 12% of $SiO_2$ and 2% of dimethicone

Commercial product: Parsol TX from DSM

Comparative Example 8e

Titanium Dioxide Comprising 7% of Aluminium Phosphate and 3% of Polyvinylpyrrolidone (PVP)

Commercial product: UV-Titan M263 from Kemira (now Sachtleben Chemie)

Comparative Example 8f

Titanium Dioxide Comprising 2.5% of $SiO_2$ and Trimethoxycaprylsilane

Commercial product: Degussa T805 from Degussa (now Evonik)

Comparative Example 8g

Titanium Dioxide Comprising $SiO_2$ and Dimethicone/Methicone Copolymer

Commercial product: T-Lite SF-S from BASF

Comparative Example 8h

Titanium Dioxide Comprising 10% of $SiO_2$

Commercial product: UV-Titan M140 from Kemira (now Sachtleben Chemie)

Comparative Example 8i

Titanium Dioxide Comprising 6% of $Al_2O_3$ and 2% of Dimethicone

Commercial product: UV-Titan M262 from Kemira (now Sachtleben Chemie)

Comparative Example 8

Titanium Dioxide Comprising 7% of $Al_2O_3$ and 11% of Methicone

Commercial product: UV-Titan M170 from Kemira (now Sachtleben Chemie)

Example 9

Experimental investigations of DHA degradation and/or discoloration of the compositions comprising DHA and titanium dioxide particles, as indicated in the tables:

The O/W test formulation described below was used in all investigations:

| Trade name | INCI | % | % |
|---|---|---|---|
| A | | | |
| $TiO_2$ according to the invention | | 5.00 | 1.00 |
| Tego Care 150 | GLYCERYL STEARATE, STEARETH-25, CETETH-20; STEARYL ALCOHOL | 8.00 | 8.00 |
| Lanette O | CETEARYL ALCOHOL | 1.50 | 1.50 |
| Tegosoft liquid | CETEARYL ETHYLHEXANOATE | 5.00 | 5.00 |
| Miglyol 812N | CAPRYC/CAPRYLIC TRIGLYVCERIDE | 5.00 | 5.00 |
| Abil-Wax 2434 | STEAROXY DIMETHICONE | 1.00 | 1.00 |
| DC 200 (100cs) | DIMETHICONE | 0.50 | 0.50 |
| Propylparaben | PROPYLPARABEN | 0.05 | 0.05 |
| B | | | |
| 1,2-Propanediol | PROPYLEN GLYCOL | 3.00 | 3.00 |
| Methylparaben | METHYL PARABEN | 0.15 | 0.15 |
| Water | AQUA | 55.80 | 62.80 |
| C | | | |
| DHA | DIHYDROXYACETONE | 5.00 | 2.00 |
| Water | AQUA | 10.00 | 10.00 |
| | | 100.00 | 100.00 |

For the storage experiment, the above-mentioned test formulation comprising 5 percent by weight of DHA is investigated together with different titanium dioxide grades. If a storage experiment relates to the test formulation comprising 2 percent by weight of DHA, this is indicated correspondingly.

DHA degradation in the test formulations investigated is determined as follows:

DHA is analysed by an enzymatic determination method and based on the following reaction:

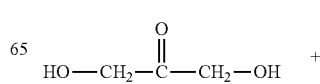

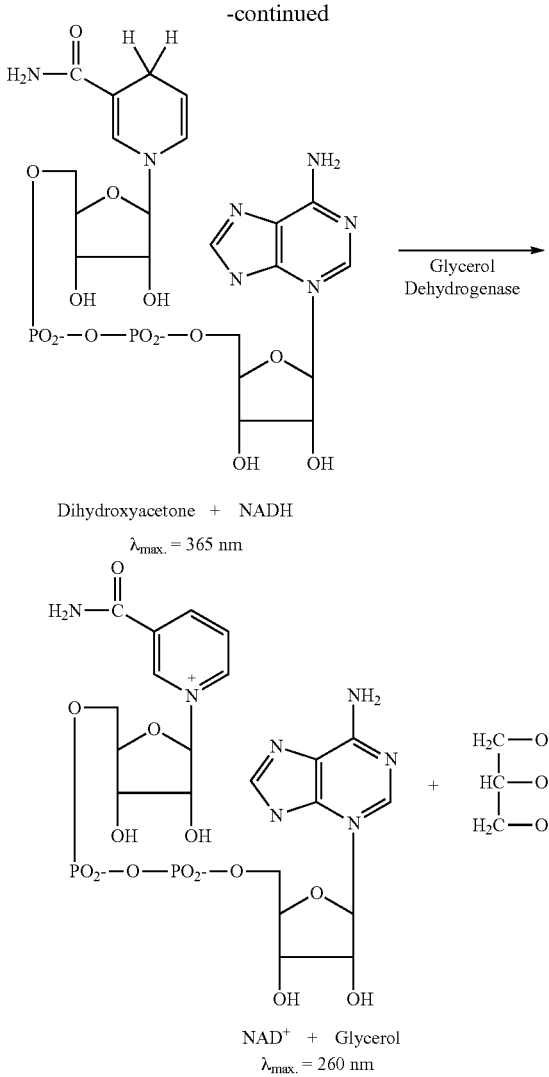

Dihydroxyacetone + NADH
$\lambda_{max.} = 365$ nm

NAD$^+$ + Glycerol
$\lambda_{max.} = 260$ nm

NADH = reduced nicotinamide adenine dinucleotide.

Reagents:

Dihydroxyacetone (Merck), glycylglycine (Merck), (NH4)$_2$SO$_4$ (Merck), sucrose (Merck), NADH-Na$_2$ (Merck), disodium hydrogenphosphate dihydrate (Merck), sodium dihydrogenphosphate dihydrate (Merck), zinc chloride (Merck), glycerol dehydrogenase (Unitika Enzyms LTD).

DHA Assay:

The determination of the DHA concentration in a formulation, based on the enzymatic DHA assay, as described below, is based on the following reaction of dihydroxyacetone:

DHA+NADH+H+→NAD++glycerol

NADH exhibits an absorption coefficient of 365 nm. The enzyme glycerol dehydrogenase catalyses the above-mentioned reaction of dihydroxyacetone with NADH. The more DHA is present, the more NADH is converted in the reaction, and the NADH absorption at 365 nm decreases.

A. Sample Buffer Solution: 1.06 g of glycylglycine, 0.42 g of (NH$_4$)$_2$SO$_4$ and 10.0 g of sucrose are dissolved in demineralised water, and the pH is adjusted to 9.0 using NaOH solution (10%), and the sample is made up to a volume of 100 ml.

B. NADH-Na$_2$ Solution: 0.060 g of NADH-Na$_2$ is dissolved in 10.0 ml of demineralised water.

C. Buffer for the Glycerol Dehydrogenase Solution:
  a. 4.43 g of disodium hydrogenphosphate,
  b. 3.90 g of sodium dihydrogenphosphate dihydrate,
  c. 100.0 g of sucrose
  d. 0.003 g of zinc chloride.

All substances mentioned are dissolved in 800 ml of demineralised water, and the solution is adjusted to a pH of 7.0 using 1 N hydrochloric acid or sodium hydroxide solution. The volume of the sample is then made up to 1000 ml using demineralised water.

D. Glycerol Dehydrogenase Solution: 10 mg of glycerol dehydrogenase in 1 ml of glycerol dehydrogenase buffer (solution C).

E. DHA Standards: 0.200 g of DHA (Art. No. 1.10150 Merck) is dissolved in 100 ml of demineralised water. This solution is diluted 1:10. The standard is prepared twice, independently of one another. The deviation of the two standards from the theoretical DHA content must be 100%+/−5%.

Sample Preparation:

0.5 g-1.0 g of the test emulsion is weighed out into a calibrated 100 ml flask. 60 ml of hot (70° C.) demineralised water is introduced, and the mixture is stirred, during which the temperature remains constant at 60° C. for 15 minutes. When the solution has cooled, the mixture is made up to the calibration mark. The solutions obtained are filtered through a membrane filter to give a clear solution. A volume of 0.1 ml of this solution is used for the DHA determination.

Measurement Conditions:

Cary 300 UV-Vis spectrophotometer (Varian) (wavelength=365 nm, d=1 cm). The reference used is demineralised water.

Pipette Procedure:

| | Blank value of solution | Sample/standard solution |
|---|---|---|
| Sample buffer | 1.00 ml | 1.00 ml |
| NADH-Na$_2$ | 0.10 ml | 0.10 ml |
| Demineralised water | 2.00 ml | 1.90 ml |
| Sample or standard | — | 0.10 ml |

The absorption of these solutions is E1 (measurement 5 minutes after mixing)

The solutions are mixed as described above and measured before the enzyme is added. For each sample, the absorbance before addition of enzyme is E1.

Subsequent addition of the glycerol dehydrogenase solution in each case 0.01 ml.

The absorption of these solutions is E2 (measurement after 15 minutes after addition of the enzyme solution).

$\Delta E = E1 - E2$
V=total volume: 3.11 ml
v=sample volume: 0.1 ml
$\varepsilon = \varepsilon(\text{NADH Na}_2) = 3.421 \cdot \text{mmol}^{-1} \cdot \text{cm}^{-1}$
MW=molecular weight (DHA): 90.08 g/mol
EW=sample solution concentration (g/l)

DHA content[% by weight in test formulation] =

$$\frac{\Delta E * V * MW * 100}{\varepsilon * d * v * 1000 * EW \text{ (g/l)}}$$

Using this enzyme-based method described, the degradation in the test formulations is determined as indicated in the following examples:

The abbreviation RT corresponds to the term room temperature.

The formulations used are stored in the dark.

Example 9A

DHA Degradation of Test Formulations

| Type of inorganic filters/DHA | Content of inorganic UV filters | DHA content | DHA content Initial value | DHA content After 3 months at RT | DHA content After 3 months at 40° C. |
|---|---|---|---|---|---|
| DHA (pure) | 0% | 5% | 4.8 | 4.7 | 4.8 |
| DHA (pure) | 0% | 2% | 2.0 | 2.0 | 1.9 |
| Parsol TX (TiO$_2$/SiO$_2$/dimethicone) | 5% | 5% | 4.7 | 3.5 | 0.9 |
| Parsol TX (TiO$_2$/SiO$_2$/dimethicone) | 1% | 2% | 2.0 | 2.2 | 1.0 |
| Sachtleben X265 (TiO$_2$/Al$_2$O$_3$/triethoxycaprylyl silane) | 5% | 5% | 5.0 | 3.0 | 0.3 |
| Sachtleben X265 (TiO$_2$/Al$_2$O$_3$/triethoxycaprylyl silane) | 1% | 2% | 1.9 | 1.6 | 0.6 |
| According to the invention (35% of SiO$_2$ + 6% of Hostaphat CC100) | 5% | 5% | 5.3 | 5.2 | 4.3 |
| According to the invention (35% of SiO$_2$ + 6% of Hostaphat CC100) | 1% | 2% | 2.0 | 2.2 | 2.0 |
| According to the invention (20% of SiO$_2$ + 6% of Hostaphat CC100) | 5% | 5% | 4.8 | 4.9 | 3.5 |
| According to the invention (20% of SiO$_2$ + 6% of Hostaphat CC100) | 1% | 2% | 2.0 | 2.2 | 1.9 |

The titanium dioxide particles from Example 3A according to the invention were hydrothermally treated in advance.

Example 9B

The test formulations investigated are numbered in the following tables, with the composition being indicated in each case. The name active compound comprising Tensan AO is 1-hydroxydodecane-1,1-diphosphonic acid, which is present in an amount of up to about 75% in the product from Polygon Chemie.

In summary, it can be stated that the titanium dioxide particles according to the invention cause significantly less DHA degradation compared with previously known compounds, as described above.

Table 1 describes the test formulations of Examples 0, 1b, 2b, 4a, 4b, 4c, 4d, 4e, 4f, 4g, 4h, 4i, 4k and 6a, with the comparative experiments being noted correspondingly. At the same time, data are indicated which indicate the DHA content after storage at 40° C. in the dark after 0.5 months, after one month and after 3 months. In the final column, the DHA degradation after 3 months at 40° C. in the dark is indicated in each case, in relation to the degradation of DHA of the same test formulation with no titanium dioxide sample (this corresponds to Example O in the table and corresponds to the test formulation of Example 9 with no titanium dioxide sample).

Table 2 describes the test formulations with Example numbers 0, 1b, 2a, 3b, 5a, 5b, 5c, 5d, 5e, 5f, 6b and 6c, with the comparative experiments being noted correspondingly. At the same time, data are indicated which indicate the DHA content after storage at 40° C. in the dark after 0.5 months, after one month and after 3 months. In the final column, the DHA degradation after 3 months at 40° C. in the dark is indicated in each case, in relation to the degradation of DHA of the same test formulation with no titanium dioxide sample.

Table 3 describes the test formulations with Example numbers 0, 4c, 5c, 5f, 7a, 7b, 8a, 8b, 8d, 8e, 8f, 8g, 8h, 8i and 8j, with the comparative experiments being noted correspondingly. At the same time, data are indicated which indicate the DHA content after storage at 40° C. in the dark after 0.5 months, after one month and after 3 months. In the final column, the DHA degradation after 3 months at 40° C. in the dark is indicated in each case, in relation to the degradation of DHA of the same test formulation with no titanium dioxide sample.

Example 9C

At the same time, it is observed that the discoloration of the test formulation due to DHA degradation after storage is significantly reduced. This is confirmed by the experimental data in the following tables:

In order to determine the Lab values, in particular the difference in the b values (delta b*), the test formulations are investigated in a Minolta Chromameter CR-400 (light type C, 2° observer).

The measurements for the calculations of delta b* and the k/s values (Tables 4 to 9) is carried out as follows:

Instruments and Reagents
1. Sample disc, plastic (own production)
2. Quartz plates
3. Colorimeter (for example X-Rite Color Eye 7000) light type C, 2° observer Procedure The sample to be measured is introduced into the sample disc [1]. It should be ensured that as far as possible no air bubbles are present in the sample.

The sample is covered with a quartz plate [2], and contact with air is thus prevented. The sample is then measured using a colorimeter [3] (light type C, 2° standard observer).

The spectral data are used to calculate the L*a*b* values [DIN 6174] and the Kubelka-Munk k/s values.

The k/s values are calculated as follows:

$k/s[\lambda] = (1-[\% \text{ remission at } \lambda]/100)^2/2\times[\% \text{ remission at } \lambda]/100$ k=absorption coefficient
s=scattering coefficient
λ=wavelength The strength of the colour reaction arises from:

colour reaction[DHA]=$k/s$[450 nm]−$k/s$[700 nm]

In general, it should be noted that the titanium dioxide particles according to the invention visually change the test formulation less, i.e. less discoloration occurs, compared with the known titanium dioxide particles of the prior art.

Table 4 describes the test formulations with Example numbers 0, 1b, 2b, 4a, 4b, 4c, 4d, 4e, 4f, 4g, 4h, 4i, 4k and 6a, with the comparative experiments being noted correspondingly. At the same time, data for delta b* and k/s values are indicated, which indicate the degree of discoloration.

Table 5 describes the test formulations with Example numbers 0, 1b, 2a, 3b, 5a, 5b, 5c, 5d, 5e, 5f, 6b and 6c, with the comparative experiments being noted correspondingly. At the same time, data for delta b* and k/s values are indicated, which indicate the degree of discoloration.

Table 6 describes the test formulations with Example numbers 0, 4c, 5c, 5f, 7a, 7b, 8a, 8b, 8d, 8e, 8f, 8g, 8h, 8i and 8j, with the comparative experiments being noted correspondingly. At the same time, data for delta b* and k/s values are indicated, which indicate the degree of discoloration.

Example 9D

Values for the test formulations which indicate the discoloration of the test formulations in the ascorbyl palmitate test, represented by the k/s values indicated, are listed below.

The ascorbyl palmitate test is carried out as follows:
Equipment
1. Watch glasses
2. Analytical balance (for example Mettler AE200)
3. Weighing brush
4. Elastic pharmacist's spatula
5. Pigment mill
6. Syringe with 0.1 ml volume graduation (for example Omnifix 2 ml)
7. Holder for quartz plate with paste,
8. Quartz plates
9. Colorimeter (for example X-rite Color Eye 7000)
Chemicals
A Ascorbyl palmitate (for example Merck material number 5.00090.9999)
B Test material (for example titanium dioxide sample)
C $C_{12}$-$C_{15}$ alkyl benzoate (for example Tegosoft TN, Evonik)
Procedure

| Weight | | |
|---|---|---|
| 0.0250 g | of ascorbyl palmitate | [A] |
| 1.000 g | of test material (for example titanium dioxide sample) | [B] |
| 0.5-4.0 ml | of $C_{12}$-$C_{15}$ alkyl benzoate | [C] |

Preparation

The ascorbyl palmitate [A] and the test material [B] are each weighed out into an appropriate watch glass [1]. 0.5 ml of $C_{12}$-$C_{15}$ alkyl benzoate [C] is placed in the centre of the lower plate of the pigment mill [5] by means of syringe [6]. The test material is added to the $C_{12}$-$C_{15}$ alkyl benzoate by means of brush [3] and formed into a paste by means of spatula [4]. If further $C_{12}$-$C_{15}$ alkyl benzoate is necessary for this purpose, it is added in 0.1 ml steps by means of syringe. The total consumption of $C_{12}$-$C_{15}$ alkyl benzoate is noted. As soon as a paste is present, the ascorbyl palmitate is added thereto by means of brush and likewise formed into a paste by means of spatula. 4 grindings are carried out without weights at 25 revolutions in each case. After each grinding, the paste is returned to the centre of the lower grinding plate by means of spatula.

The sample is subsequently introduced into a sample can and thus placed in the dark in order that no reaction with daylight takes place which could falsify the measurement values.

Measurement

The spectral data are measured after storage in the dark for 24 h after preparation.

To this end, the sample batch is stirred up homogeneously using a spatula and placed in the centre of the quartz plate [8]. The quartz plate is provided with a holder [7] for the measurement. The sample is then measured using a colorimeter [9] (no gloss, with UV, light type C, 2° standard observer).

The operation of the colorimeter is assumed to be known or is indicated in the corresponding operating manual.

Evaluation

The spectral data are used to calculate the L*a*b* values and the k/s values. The k/s values are calculated as follows:

$$k/s[\alpha] = (1-[\% \text{ remission at } \lambda]/100)^2 / 2 \times [\% \text{ remission at } \lambda]/100$$

k=absorption coefficient
s=scattering coefficient
λ=wavelength

The strength of the interaction with ascorbyl palmitate arises from:

$$\text{Interaction[ascorbyl palmitate]} = k/s[430 \text{ nm}] - k/s[700 \text{ nm}]$$

k/s [700 nm] is the range in which no interactions with ascorbyl palmitate occur. In order to take into account the contributions of the sample tested and the $C_{12}$-$C_{15}$ alkyl benzoate to the k/s value, this value is subtracted and functions as base line.

Table 7 describes the test formulations with example numbers 0, 1b, 2b, 4a, 4b, 4c, 4d, 4e, 4f, 4g, 4h, 4i, 4k and 6a, with the comparative experiments being noted correspondingly. At the same time, the k/s values determined are indicated, which indicate the discoloration in the ascorbyl palmitate test after 24 hours.

Table 8 describes the test formulations with example numbers 0, 1b, 2a, 3b, 5a, 5b, 5c, 5d, 5e, 5f, 6b and 6c, with the comparative experiments being noted correspondingly. At the same time, the k/s values determined are indicated, which indicate the discoloration in the ascorbyl palmitate test after 24 hours.

Table 9 describes the test formulations with example numbers 0, 4c, 5c, 5f, 7a, 7b, 8a, 8b, 8d, 8e, 8f, 8g, 8h, 8i and 8j, with the comparative experiments being noted correspondingly. At the same time, the k/s values determined are indicated, which indicate the discoloration in the ascorbyl palmitate test after 24 hours.

TABLE 1

| Example No. | | HT | % SiO2 | % phosphoric acid monocetyl ester (C16) [Hostaphat CC100] | % phosphoric acid mono- and di-stearyl ester mixture [Hostaphat CS120] | % 1-hydroxyethane-1,1-diphosphonic acid [Cublen K 60] | 2-Phosphono-butane-1,2,4-tricarboxylic acid [Cublen P 50] | % aminotrismethylene-phosphonic acid [Cublen AP 5] | % laurylphosphonic acid (Rhodia) | % octylphosphonic acid (Rhodia) | % active compound from Tensan AO |
|---|---|---|---|---|---|---|---|---|---|---|---|
| 0 | | — | — | — | — | — | — | — | — | — | — |
| 1b | Comp. Example | no | — | — | — | — | — | — | — | — | — |
| 2b | Comp. Example | no | 35 | — | — | — | — | — | — | — | — |
| 4a | | no | 35 | 5 | — | — | — | — | — | — | — |
| 4b | | no | 35 | 10 | — | — | — | — | — | — | — |
| 4c | | no | 35 | 15 | — | — | — | — | — | — | — |
| 4d | | no | 35 | — | 15 | — | — | — | — | — | — |
| 4e | | no | 35 | — | — | 15 | — | — | — | — | — |
| 4f | | no | 35 | — | — | — | 15 | — | — | — | — |
| 4g | | no | 35 | — | — | — | — | 15 | — | — | — |
| 4h | | no | 35 | — | — | — | — | — | 15 | — | — |
| 4i | | no | 35 | — | — | — | — | — | — | 15 | — |
| 4k | | no | 35 | — | — | — | — | — | — | — | 5 |
| 6a | Comp. Example | no | 20 | — | — | — | — | — | — | — | — |

| Example No. | | % simethicone | DHA content not stored | DHA content after 0.5 months at 40° C. | DHA content after 1 months at 40° C. | DHA content after 3 months at 40° C. | DHA degradation after 0.5 months at 40° C. | DHA degradation after 1 months at 40° C. | DHA degradation after 3 months at 40° C. | DHA degrad. after 3 months at 40° C. [ref. deg. DHA with no TiO2 sample] |
|---|---|---|---|---|---|---|---|---|---|---|
| 0 | | — | 5.8% | 5.5% | 5.5% | 4.8% | 5% | 5% | 17% | 0% |
| 1b | Comp. Example | — | 5.7% | 0.3% | 0.0% | 0.0% | 96% | 100% | 100% | 83% |
| 2b | Comp. Example | — | 5.7% | 2.9% | 2.1% | 1.1% | 49% | 63% | 81% | 63% |
| 4a | | — | 6.0% | 4.1% | 3.0% | 2.0% | 32% | 50% | 67% | 49% |
| 4b | | — | 5.7% | 5.4% | 5.0% | 4.3% | 5% | 12% | 25% | 7% |
| 4c | | — | 5.9% | 5.6% | 5.2% | 4.4% | 5% | 12% | 25% | 8% |
| 4d | | — | 5.9% | 5.7% | 5.4% | 4.4% | 3% | 8% | 25% | 8% |
| 4e | | — | 5.7% | 5.4% | 5.5% | 4.0% | 5% | 4% | 30% | 13% |
| 4f | | — | 5.7% | 5.1% | 5.1% | 3.8% | 11% | 11% | 33% | 16% |
| 4g | | — | 5.7% | 5.3% | 5.4% | 4.2% | 7% | 5% | 33% | 16% |
| 4h | | — | 5.7% | 5.6% | 5.1% | 4.2% | 2% | 11% | 26% | 9% |
| 4i | | — | 5.7% | 5.2% | 5.4% | 3.8% | 9% | 14% | 26% | 9% |
| 4k | | — | 5.7% | 5.2% | 4.9% | 3.8% | 9% | 14% | 33% | 16% |
| 6a | Comp. Example | 10 | 5.7% | 3.7% | 3.1% | 2.0% | 35% | 46% | 65% | 48% |

TABLE 2

DHA content after storage at 40° C. (dark)

| Example No. | | HT | % SiO2 | % phosphoric acid monocetyl ester (C16) [Hostaphat CC100] | % simethicone | DHA content not stored | DHA content after 0.5 months at 40° C. | DHA content after 1 months at 40° C. |
|---|---|---|---|---|---|---|---|---|
| 0 | | — | — | — | — | 5.8% | 5.5% | 5.5% |
| 1b | Comp. Example | no | — | — | — | 5.7% | 0.3% | 0.0% |
| 2a | Comp. Example | yes | 20 | — | — | 6.1% | 4.6% | 3.8% |
| 3b | Comp. Example | yes | 35 | — | — | 5.7% | 4.5% | 4.2% |
| 5a | | yes | 20 | 3 | — | 5.7% | — | 3.5% |
| 5b | | yes | 20 | 6 | — | 4.9% | 4.7% | 4.8% |
| 5c | | yes | 20 | 9 | — | 5.7% | — | 4.6% |
| 5d | | yes | 35 | 3 | — | 5.7% | 3.0% | 2.8% |
| 5e | | yes | 35 | 6 | — | 5.4% | 5.2% | 5.2% |
| 5f | | yes | 35 | 9 | — | 5.7% | 4.8% | 4.7% |
| 6b | Comp. Example | yes | 20 | — | 10 | 5.7% | 3.9% | 3.1% |
| 6c | Comp. Example | yes | 35 | — | 10 | 5.7% | 4.6% | 4.2% |

| Example No. | | DHA content after 3 months at 40° C. | DHA degradation after 0.5 months at 40° C. | DHA degradation after 1 months at 40° C. | DHA degradation after 3 months at 40° C. | DHA degrad. after 3 months at 40° C. [ref. deg. DHA with no TiO2 sample] |
|---|---|---|---|---|---|---|
| 0 | | 4.8% | 5% | 5% | 17% | 0% |
| 1b | Comp. Example | 0.0% | 96% | 100% | 100% | 83% |
| 2a | Comp. Example | 2.4% | 25% | 38% | 61% | 43% |
| 3b | Comp. Example | 3.6% | 21% | 26% | 37% | 20% |
| 5a | | 2.8% | — | 39% | 51% | 34% |
| 5b | | 4.0% | 4% | 2% | 18% | 1% |
| 5c | | 4.7% | — | 19% | 18% | 0% |
| 5d | | 2.1% | 47% | 51% | 63% | 46% |
| 5e | | 4.4% | 4% | 4% | 19% | 1% |
| 5f | | 4.3% | 16% | 18% | 25% | 7% |
| 6b | Comp. Example | 1.7% | 32% | 46% | 70% | 53% |
| 6c | Comp. Example | 3.7% | 19% | 26% | 35% | 18% |

TABLE 3

DHA content after storage at 40° C. (dark)

| | Selection | Example No. | HT | SiO2 | % phosphoric acid monocetyl ester (C16) [Hostaphat CC100] | % octylphosphonic acid (Rhodia) | % Al2O3 | Coating | DHA content not stored |
|---|---|---|---|---|---|---|---|---|---|
| | yes | 0 | — | — | — | | | | 5.8% |
| | yes | 4c | no | 35 | 15 | | | | 5.9% |
| | yes | 5c | yes | 20 | 9 | | | | 5.7% |
| | yes | 5f | yes | 35 | 9 | | | | 5.7% |
| | yes | 7a | no | | | 10 | 12 | | 5.7% |
| Eusolex T-S | yes | 7b | no | | | | 12 | 10% stearic acid | 5.7% |
| UV-Titan X195 | yes | 8a | no | 10 | | | | 9% methicone | 5.7% |
| UV-Titan M195 | yes | 8b | no | 10 | | | | 9% methicone | 5.0% |
| Parsol TX | yes | 8d | no | 12 | | | | 2% dimethicone | 5.2% |
| UV-Titan M263 | yes | 8e | no | | | | | 7% Al phosphate + 3% PVP | 5.7% |
| Degussa T805 | yes | 8f | no | 2.5 | | | | Trimethoxycaprylsilane | 5.7% |
| T-Lite SF-S | yes | 8g | no | X | | | X | Dimethicone/methicone copolymer | 5.1% |
| UV-Titan M140 | yes | 8h | no | 10 | | | | | 4.9% |
| UV-Titan M262 | yes | 8i | no | | | | 6 | 2% dimethicone | 4.8% |
| UV-Titan M170 | yes | 8j | no | | | | 7 | 11% methicone | 4.9% |

| | | DHA content after 0.5 months at 40° C. | DHA content after 1 months at 40° C. | DHA content after 3 months at 40° C. | DHA degradation after 0.5 months at 40° C. | DHA degradation after 1 months at 40° C. | DHA degradation after 3 months at 40° C. | DHA degradation after 3 months at 40° C. [ref. degrad. of DHA with no TiO2 sample] |
|---|---|---|---|---|---|---|---|---|
| | | 5.5% | 5.5% | 4.8% | 5% | 5% | 17% | 0% |
| | | 5.6% | 5.2% | 4.4% | 5% | 12% | 25% | 8% |
| | | — | 4.6% | 4.7% | — | 19% | 18% | 0% |
| | | 4.8% | 4.7% | 4.3% | 16% | 18% | 25% | 7% |
| | Eusolex T-S | 5.5% | 5.2% | 4.6% | 4% | 9% | 19% | 2% |
| | UV-Titan X195 | 3.2% | 1.6% | 0.4% | 44% | 72% | 93% | 76% |

TABLE 3-continued

| | | | | | | | |
|---|---|---|---|---|---|---|---|
| UV-Titan M195 | 3.5% | 2.8% | 1.8% | 39% | 51% | 68% | 51% |
| Parsol TX | 3.6% | 2.8% | 1.7% | 28% | 44% | 66% | 49% |
| UV-Titan M263 | 3.5% | 2.8% | 1.8% | 33% | 46% | 65% | 48% |
| Degussa T805 | 2.7% | 1.7% | 0.3% | 53% | 70% | 96% | 78% |
| T-Lite SF-S | 4.6% | 3.7% | 1.7% | 19% | 35% | 70% | 53% |
| | 3.4% | 2.3% | | 33% | 55% | 86% | 69% |
| UV-Titan M140 | 2.1% | 1.3% | 0.3% | 57% | 73% | 95% | 78% |
| UV-Titan M262 | 2.4% | 1.6% | 0.3% | 50% | 67% | 95% | 78% |
| UV-Titan M170 | 2.6% | 1.3% | 0.3% | 47% | 73% | 95% | 78% |

TABLE 4

Discoloration due to DHA degradation after storage at 40° C. (dark)

| Example No. | | HT | % SiO2 | % phosphoric acid monoetyl cester (C16) [Hostaphat CC100] | % phosphoric acid mono- and di-stearyl ester mixture [Hostaphat CS120] | % 1-hydroxyethane-1,1-diphosphonic acid [Cublen K 60] | 2-Phosphono-butane-1,2,4-tricarboxylic acid [Cublen P 50] | % amino-trismethylene phosphonic acid [Cublen AP5] | % lauryl-phosphonic acid (Rhodia) | % octyl-phosphonic acid (Rhodia) |
|---|---|---|---|---|---|---|---|---|---|---|
| 0 | | — | — | — | — | — | — | — | — | — |
| 1b | Comp. Example | no | — | — | — | — | — | — | — | — |
| 2b | Comp. Example | no | 35 | — | — | — | — | — | — | — |
| 4a | | no | 35 | 5 | — | — | — | — | — | — |
| 4b | | no | 35 | 10 | — | — | — | — | — | — |
| 4c | | no | 35 | 15 | — | — | — | — | — | — |
| 4d | | no | 35 | — | 15 | — | — | — | — | — |
| 4e | | no | 35 | — | — | 15 | — | — | — | — |
| 4f | | no | 35 | — | — | — | 15 | — | — | — |
| 4g | | no | 35 | — | — | — | — | 15 | — | — |
| 4h | | no | 35 | — | — | — | — | — | 15 | — |
| 4i | | no | 35 | — | — | — | — | — | — | 15 |
| 4k | | no | 35 | — | — | — | — | — | — | — |
| 6a | Comp. Example | no | 20 | — | — | — | — | — | — | — |

| Example No. | | % active compound | % simeth-icone | delta b* not stored | delta b* after 0.5 months at 40° C. | delta b* after 1 months at 40° C. | delta b* after 3 months at 40° C. | k/s values not stored | k/s values after 0.5 months at 40° C. | k/s values after 1 months at 40° C. | k/s values after 3 months at 40° C. |
|---|---|---|---|---|---|---|---|---|---|---|---|
| 0 | | — | — | 0 | -0.4 | -0.3 | 0.7 | -0.04 | -0.05 | -0.05 | -0.04 |
| 1b | Comp. Example | — | — | 0 | 7.0 | 8.6 | 11.5 | 0.37 | 2.02 | 2.42 | 3.80 |
| 2b | Comp. Example | — | — | 0 | 7.7 | 10.4 | 17.6 | -0.02 | 0.11 | 0.21 | 0.50 |
| 4a | | — | — | 0 | 3.2 | 5.8 | 13.7 | 0.00 | 0.04 | 0.09 | 0.39 |
| 4b | | — | — | 0 | 2.2 | 3.0 | 5.6 | 0.00 | 0.02 | 0.03 | 0.08 |
| 4c | | — | — | 0 | 0.5 | 1.1 | 2.1 | 0.01 | 0.01 | 0.02 | 0.03 |
| 4d | | — | — | 0 | 1.0 | 2.0 | 1.1 | 0.00 | 0.00 | 0.02 | 0.01 |
| 4e | | — | — | 0 | 0.5 | 2.0 | 2.8 | -0.01 | 0.00 | 0.01 | 0.01 |
| 4f | | — | — | 0 | 1.3 | 1.5 | 3.0 | -0.01 | 0.01 | 0.01 | 0.02 |
| 4g | | — | — | 0 | 0.3 | 4.2 | 10.0 | 0.00 | 0.00 | 0.03 | 0.10 |
| 4h | | — | — | 0 | 0.4 | 1.9 | 3.8 | 0.00 | 0.01 | 0.02 | 0.04 |
| 4i | | — | — | 0 | 0.2 | -0.1 | 2.1 | 0.01 | 0.01 | 0.01 | 0.03 |
| 4k | | 5 | — | 0 | 0.7 | 1.9 | 6.4 | 0.00 | 0.01 | 0.02 | 0.10 |
| 6a | Comp. Example | — | 10 | 0 | 8.3 | 16.3 | 23.2 | -0.02 | 0.13 | 0.31 | 1.10 |

TABLE 5

Discoloration due to DHA degradation after storage at 40° C. (dark)

| Example No. | | HT | % SiO2 | % phosphoric acid monoetyl ester (C16) [Hostaphat CC100] | % simethicone | delta b* not stored | delta b* after 0.5 months at 40° C. | delta b* after 1 months at 40° C. |
|---|---|---|---|---|---|---|---|---|
| 0 | | — | — | — | — | 0 | -0.4 | -0.3 |
| 1b | Comp. Example | no | — | — | — | 0 | 7.0 | 8.6 |
| 2a | Comp. Example | yes | 20 | — | — | 0 | 3.0 | 5.4 |

TABLE 5-continued

Discoloration due to DHA degradation after storage at 40° C. (dark)

| 3b | Comp. Example | yes | 35 | — | — | 0 | 2.3 | 3.4 |
|---|---|---|---|---|---|---|---|---|
| 5a |  | yes | 20 | 3 | — | 0 | 2.5 | 5.0 |
| 5b |  | yes | 20 | 6 | — | 0 | 0.1 | 0.8 |
| 5c |  | yes | 20 | 9 | — | 0 | 0.0 | 0.9 |
| 5d |  | yes | 35 | 3 | — | 0 | 2.5 | 4.8 |
| 5e |  | yes | 35 | 6 | — | 0 | −0.3 | 0.8 |
| 5f |  | yes | 35 | 9 | — | 0 | 1.5 | 2.3 |
| 6b | Comp. Example | yes | 20 |  | 10 | 0 | 6.7 | 9.1 |
| 6c | Comp. Example | yes | 35 |  | 10 | 0 | 2.2 | 3.1 |

| Example No. |  | delta b* after 3 months at 40° C. | not stored | k/s values after 0.5 months at 40° C. | k/s values after 1 months at 40° C. | k/s values after 3 months at 40° C. |
|---|---|---|---|---|---|---|
| 0 |  | 0.7 | −0.04 | −0.05 | −0.05 | −0.04 |
| 1b | Comp. Example | 11.5 | 0.37 | 2.02 | 2.42 | 3.80 |
| 2a | Comp. Example | 10.6 | −0.01 | 0.02 | 0.06 | 0.16 |
| 3b | Comp. Example | 8.9 | −0.01 | 0.01 | 0.02 | 0.079 |
| 5a |  | 13.4 | −0.01 | 0.01 | 0.04 | 0.22 |
| 5b |  | 1.4 | −0.01 | −0.01 | −0.01 | 0.00 |
| 5c |  | 0.8 | 0.00 | 0.00 | 0.01 | −0.03 |
| 5d |  | 12.6 | −0.01 | 0.01 | 0.04 | 0.22 |
| 5e |  | −1.7 | −0.01 | −0.01 | 0.00 | 0.01 |
| 5f |  | 1.3 | −0.01 | 0.00 | 0.01 | −0.01 |
| 6b | Comp. Example | 18.1 | −0.01 | 0.08 | 0.12 | 0.47 |
| 6c | Comp. Example | 8.8 | −0.02 | 0.00 | 0.01 | 0.072 |

TABLE 6

Discoloration due to DHA degradation after storage at 40° C. (dark)

|  | Selection | Example No. | HT | % SiO2 | % phosphoric acid monocetyl ester (C16) [Hostaphat CC100] | % octyl-phosphonic acid (Rhodia) | % Al2O3 | Coating | delta b* not stored | delta b* after 0.5 months at 40° C. |
|---|---|---|---|---|---|---|---|---|---|---|
|  | yes | 0 |  | — | — |  |  |  | 0 | −0.4 |
|  | yes | 4c | no | 35 | 15 |  |  |  | 0 | 0.5 |
|  | yes | 5c | yes | 20 | 9 |  |  |  | 0 | 0.0 |
|  | yes | 5f | yes | 35 | 9 |  |  |  | 0 | 1.5 |
|  | yes | 7a | no |  |  | 10 | 12 |  | 0 | −1.3 |
| Eusolex T-S | yes | 7b | no |  |  |  | 12 | 10% stearic acid | 0 | 9.5 |
| UV-Titan X195 | yes | 8a | no | 10 |  |  |  | 9% methicone | 0 | 5.6 |
| UV-Titan M195 | yes | 8b | no | 10 |  |  |  | 9% methicone | 0 | 5.1 |
| Parsol TX | yes | 8d | no | 12 |  |  |  | 2% dimethicone | 0 | 6.4 |
| UV-Titan M263 | yes | 8e | no |  |  |  |  | 7% Al phosphate + 3% PVP | 0 | 4.6 |
| Degussa T805 | yes | 8f | no | 2.5 |  |  |  | Trimethoxy-caprylsilane | 0 | 2.9 |
| T-Lite SF-S | yes | 8g | no | X |  |  | X | Dimethicone/methicone copolymer | 0 | 2.9 |
| UV-Titan M140 | yes | 8h | no | 10 |  |  |  |  | 0 | 17.0 |
| UV-Titan M262 | yes | 8i | no |  |  |  | 6 | 2% dimethicone | 0 | 6.4 |
| UV-Titan M170 | yes | 8j | no |  |  |  | 7 | 11% methicone | 0 | 11.9 |

|  | delta b* after 1 months at 40° C. | delta b* after 3 months at 40° C. | not stored | k/s values after 0.5 months at 40° C. | k/s values after 1 months at 40° C. | k/s values after 3 months at 40° C. |
|---|---|---|---|---|---|---|
|  | −0.3 | 0.7 | −0.04 | −0.05 | −0.05 | −0.04 |
|  | 1.1 | 2.1 | 0.01 | 0.01 | 0.02 | 0.03 |
|  | 0.9 | 0.8 | 0.00 | 0.00 | 0.01 | −0.03 |
|  | 2.3 | 1.3 | −0.01 | 0.00 | 0.01 | −0.01 |
|  | −2.4 | 0.1 | 0.02 | −0.01 | −0.03 | 0.00 |
| Eusolex T-S | 14.5 | 23.5 | 0.01 | 0.21 | 0.59 | 2.67 |
| UV-Titan X195 | 11.3 | 19.1 | 0.00 | 0.06 | 0.18 | 0.61 |
| UV-Titan M195 | 8.1 | 14.3 | −0.01 | 0.04 | 0.10 | 0.30 |
| Parsol TX | 9.9 | 15.7 | 0.00 | 0.07 | 0.14 | 0.40 |
| UV-Titan M263 | 11.9 | 21.7 | 0.00 | 0.04 | 0.16 | 0.90 |
| Degussa T805 | 7.6 | 13.3 | 0.00 | 0.03 | 0.12 | 0.37 |
| T-Lite SF-S | 12.2 | 26.5 | 0.00 | 0.03 | 0.20 | 1.25 |
| UV-Titan M140 | 23.0 | 27.1 | −0.02 | 0.59 | 1.30 | 4.13 |

TABLE 6-continued

Discoloration due to DHA degradation after storage at 40° C. (dark)

| UV-Titan M262 | 11.8 | 20.2 | 0.00 | 0.06 | . | 0.88 |
| UV-Titan M170 | 18.8 | 25.4 | 0.00 | 0.25 | 0.81 | 2.52 |

TABLE 7

Discoloration ascorbyl palmitate test after 24 h

| Example No. | | % SiO2 | % phosphoric acid monocetyl ester (C16) [Hostaphat CC100] | % phosphoric acid mono- and di-stearyl ester mixture [Hostaphat CS 120] | % 1-hydroxyethane-1,1-diphosphonic acid [Cublen K 60] | 2-Phosphono-butane-1,2,4-tricarboxylic acid [Cublen P 50] | % amino-trismethylene-phosphonic acid [Cublen AP 5] | % lauryl-phosphonic acid (Rhodia) |
|---|---|---|---|---|---|---|---|---|
| 0 | | — | — | — | — | — | — | — |
| 1b | Comp. Example | no | — | — | — | — | — | — |
| 2b | Comp. Example | no | 35 | — | — | — | — | — | — |
| 4a | | no | 35 | 5 | — | — | — | — | — |
| 4b | | no | 35 | 10 | — | — | — | — | — |
| 4c | | no | 35 | 15 | — | — | — | — | — |
| 4d | | no | 35 | — | 15 | — | — | — | — |
| 4e | | no | 35 | — | — | 15 | — | — | — |
| 4f | | no | 35 | — | — | — | 15 | — | — |
| 4g | | no | 35 | — | — | — | — | 15 | — |
| 4h | | no | 35 | — | — | — | — | — | 15 |
| 4i | | no | 35 | — | — | — | — | — | — |
| 4k | | no | 35 | — | — | — | — | — | — |
| 6a | Comp. Example | no | 20 | — | — | — | — | — | — |

| Example No. | | % octyl-phosphonic acid (Rhodia) | % active compound from Tensan AO | % simethicone | Ascorbyl palmitate test k/s [430 nm] | Ascorbyl palmitate test k/s [750 nm] | Ascorbyl palmitate test k/s [430 nm-750 nm] |
|---|---|---|---|---|---|---|---|
| 0 | | — | — | — | — | — | — |
| 1b | Comp. Example | — | — | — | 2.92 | 0.23 | 2.69 |
| 2b | Comp. Example | — | — | — | 0.67 | 0.11 | 0, .6 |
| 4a | | — | — | — | 0.64 | 0.10 | 0.54 |
| 4b | | — | — | — | 0.38 | 0.09 | 0.29 |
| 4c | | — | — | — | 0.47 | 0.13 | 0.34 |
| 4d | | — | — | — | 0.25 | 0.07 | 0.18 |
| 4e | | — | — | — | 0.15 | 0.08 | 0.07 |
| 4f | | — | — | — | 0.21 | 0.07 | 0.14 |
| 4g | | — | — | — | 0.18 | 0.07 | 0.11 |
| 4h | | — | — | — | 0.18 | 0.08 | 0.10 |
| 4i | | 15 | — | — | 0.15 | 0.08 | 0.08 |
| 4k | | — | 5 | — | 0.33 | 0.08 | 0.25 |
| 6a | Comp. Example | — | — | 10 | 0.81 | 0.11 | 0.69 |

TABLE 8

Discoloration ascorbyl palmitate test after 24 h

| Example No. | | HT | % SiO2 | % phosphoric acid monocetyl ester (C16) [Hostaphat CC100] | % simethicone | Ascorbyl palmitate test k/s [430 nm] | Ascorbyl palmitate test k/s [750 nm] | Ascorbyl palmitate test k/s [430 nm-750 nm] |
|---|---|---|---|---|---|---|---|---|
| 0 | | — | — | — | — | — | — | — |
| 1b | Comp. Example | no | — | — | — | 2.92 | 0.23 | 2.69 |
| 2a | Comp. Example | yes | 20 | — | — | — | — | — |
| 3b | Comp. Example | yes | 35 | — | — | 0.35 | 0.12 | 0.24 |
| 5a | | yes | 20 | 3 | — | 0.38 | 0.10 | 0.28 |
| 5b | | yes | 20 | 6 | — | 0.22 | 0.08 | 0.13 |
| 5c | | yes | 20 | 9 | — | 0.20 | 0.09 | 0.11 |
| 5d | | yes | 35 | 3 | — | 0.34 | 0.08 | 0.25 |

TABLE 8-continued

Discoloration ascorbyl palmitate test after 24 h

| Example No. | HT | % SiO2 | % phosphoric acid monocetyl ester (C16) [Hostaphat CC100] | % simethicone | Ascorbyl palmitate test k/s [430 nm] | Ascorbyl palmitate test k/s [750 nm] | Ascorbyl palmitate test k/s [430 nm-750 nm] |
|---|---|---|---|---|---|---|---|
| 5e | | yes | 35 | 6 | — | 0.11 | 0.10 | 0.02 |
| 5f | | yes | 35 | 9 | — | 0.20 | 0.09 | 0.11 |
| 6b | Comp. Example | yes | 20 | — | 10 | 0.61 | 0.11 | 0.50 |
| 6c | Comp. Example | yes | 35 | — | 10 | 0.22 | 0.13 | 0.10 |

TABLE 9

Discoloration ascorbyl palmitate test after 24 h

| | Example No. | HT | % SiO2 | % phosphoric acid monocetyl ester (C16) [Hostaphat CC100] | % octyl-phosphonic acid (Rhodia) | % Al2O3 | Coating | Ascorbyl palmitate test k/s [430 nm] | Ascorbyl palmitate test k/s [750 nm] | Ascorbyl palmitate test k/s [430 nm-750 nm] |
|---|---|---|---|---|---|---|---|---|---|---|
| | 0 | — | — | — | | | | — | — | — |
| | 4c | no | 35 | 15 | | | | 0.47 | 0.13 | 0.34 |
| | 5c | yes | 20 | 9 | | | | 0.20 | 0.09 | 0.11 |
| | 5f | yes | 35 | 9 | | | | 0.20 | 0.09 | 0.11 |
| | 7a | no | | | 10 | 12 | | 0.13 | 0.07 | 0.06 |
| Eusolex T-S | 7b | no | | | | 12 | 10% stearic acid | 0.82 | 0.12 | 0.70 |
| UV-Titan X195 | 8a | no | 10 | | | | 9% methicone | — | — | — |
| UV-Titan M195 | 8b | no | 10 | | | | 9% methicone | 2.92 | 0.23 | 2.69 |
| Parsol TX | 8d | no | 12 | | | | 2% dimethicone | — | — | — |
| UV-Titan M263 | 8e | no | | | | | 7% Al phosphate + 3% PVP | 0.14 | 0.09 | 0.05 |
| Degussa T805 | 8f | no | 2.5 | | | | Trimethoxycaprylsilane | 1.56 | 0.15 | 1.41 |
| T-Lite SF-S | 8g | no | X | | | X | Dimethicone/methicone copolymer | 0.39 | 0.11 | 0.28 |
| UV-Titan M140 | 8h | no | 10 | | | | | — | — | — |
| UV-Titan M262 | 8i | no | | | | 6 | 2% dimethicone | — | — | — |
| UV-Titan M170 | 8j | no | | | | 7 | 11% methicone | — | — | — |

Recipe Example 1

Sun Protection Soft Creme (O/W)

| Raw material (INCI) | % by wt. |
|---|---|
| A | |
| Titanium dioxide according to the invention | 3.00 |
| Steareth-10, Steareth-7, Stearyl alcohol | 2.00 |
| Glyceryl stearate, Ceteth-20 | 2.00 |
| Glyceryl stearate | 3.00 |
| Microwax | 1.00 |
| Oleyl oleate | 6.00 |
| Cetearyl octanoate | 14.00 |
| Caprylic/capric triglyceride | 4.00 |
| Propylparaben | 0.05 |
| B | |
| Propylene glycol | 4.00 |
| Allantoin | 0.20 |
| Water | 60.60 |
| Methylparaben | 0.15 |

Preparation

Heat phase A and phase B to 80° C. Slowly add phase B to phase A with stirring, homogenise and cool with stirring.

Recipe Example 2

Sun Protection Soft Creme (O/W)

| Raw material (INCI) | % |
|---|---|
| A | |
| Titanium dioxide according to the invention | 10.00 |
| Steareth-10, steareth-7, stearyl alcohol | 3.00 |
| Glyceryl stearate, ceteth-20 | 3.00 |
| Glyceryl stearate | 3.00 |
| Microwax | 1.00 |
| Oleyl oleate | 4.00 |
| Cetearyl octanoate | 10.50 |
| Caprylic/capric triglyceride | 4.00 |
| Propylparaben | 0.05 |
| B | |
| Propylene glycol | 4.00 |
| Allantoin | 0.20 |
| Water | 57.10 |
| Methylparaben | 0.15 |

Preparation

Heat phase A and B to 80° C. Slowly add phase B to phase A with stirring, homogenise and cool with stirring.

Recipe Example 3

Sun Protection Lotion (O/W)

| Raw material (INCI) | % |
| --- | --- |
| A | |
| Octocrylene | 6.00 |
| Butyl methoxydibenzoylmethane | 2.00 |
| Polyglyceryl-3 methylglucose distearate | 4.00 |
| Ethylhexyl stearate | 8.00 |
| Cetearyl isononanoate | 2.00 |
| PVP/eicosene copolymer | 1.00 |
| Tocopheryl acetate | 1.00 |
| B | |
| Xanthan gum | 0.30 |
| Sodium cetearyl sulfate | 1.00 |
| Glycerin | 5.00 |
| Water | 65.70 |
| C | |
| Titanium dioxide according to the invention | 4.00 |
| D | |
| Phenoxyethanol, butylparaben, ethylparaben, propylparaben, methylparaben | 1.00 |

Preparation

Heat phase A to 80° C. Pre-swell the Keltrol of phase B in the water, then add the remaining raw materials and heat to 80° C. Add phase A to phase B and homogenise for 2 min. (stick-type mixer): cool with stirring and add phase C at 35° C. Homogenise again for 1 min. (stick-type mixer). Cool to room temperature and stir in phase D.

Recipe Example 4

Sun Protection Lotion (O/W)

| A | |
| --- | --- |
| Steareth-10, steareth-7, stearyl alcohol | 3.00 |
| Glyceryl stearate, ceteth-20 | 3.00 |
| Cetearyl octanoate | 13.00 |
| Glyceryl stearate | 3.00 |
| Oleyl oleate | 7.00 |
| Microwax | 1.00 |
| Caprylic/capric triglyceride | 6.00 |
| Preservative | q.s. |
| Butyl Methoxydibenzoylmethane | 2.00 |
| B | |
| 33% aqueous dispersion of the titanium dioxide according to the invention | 16.70 |
| Propylene glycol | 4.00 |
| Allantoin | 0.20 |
| Water | to 100 |
| Preservative | q.s. |
| C | |
| Water | 10.00 |
| Dihydroxyacetone | 4.00 |

Preparation

Heat phase A to 75° C. and phase B to 80° C. Slowly stir phase B into phase A. Homogenise and cool with stirring.

Recipe Example 5

Sun Protection Spray Lotion (O/W)

| A | |
| --- | --- |
| Titanium dioxide according to the invention | 5.00 |
| Ethylhexyl methoxycinnamate, BHT | 7.50 |
| Benzophenone-3 | 2.50 |
| PEG-100 stearate, glyceryl stearate | 2.80 |
| PPG-1-PEG-9 lauryl glycol ether | 0.40 |
| Dicapryl ether | 4.50 |
| Steareth-10 | 0.50 |
| Stearyl alcohol | 0.60 |
| Dimethicone | 2.00 |
| B | |
| Dimethicone copolyol phosphate | 2.50 |
| Chitosan glycolate | 2.00 |
| Glycerin | 2.50 |
| Water | ad 100 |
| C | |
| PPG-1 trideceth-6, polyquaternium-37, propylene glycol dicaprylate/dicaprate | 0.40 |
| D | |
| Preservative | q.s. |
| Water demineralised | 10.00 |
| Dihydroxyacetone | 3.00 |

Preparation

Combine phase A apart from the titanium dioxide and heat to 60° C. Slowly incorporate titanium dioxide into the molten oil phase. Heat phase B-1 to 60° C., then disperse in phase B-2 with stirring. Stir phase A into phase B with high energy input. Cool with stirring, and add phase C at 40° C. Homogenise and add phase D with stirring.

Recipe Example 6

Sun Protection Spray with Tanning Intensification

| | | |
| --- | --- | --- |
| A) | CERALUTION ® C; Sasol | 15.0% |
| B) | Titanium dioxide according to the invention | 5.0% |
| | Ethylhexyl Methoxycinnamate | 4.8% |
| | Ethylhexyl Salicylate | 4.8% |
| | Tocopheryl Acetate | 0.6% |
| | Cyclomethicone | 1.0% |
| | C12-15 Alkyl Benzoate | 2.5% |
| | Tridecyl Salicylate | 2.5% |
| C) | Dihydroxyacetone | 3% |
| | Water (Aqua), Deionised | to 100 |
| | Water (Aqua), Deionised with 4% of Avicel CL 611 (Microcrystalline Cellulose (and) Cellulose Gum) | 25.0% |
| D) | Preservative | q.s. |

Preparation

Phase B is slowly added to phase A at room temperature with stirring. Phase C is then added. Phase D subsequently added.

INCI CERALUTION® C:

Aqua (and) Capric/Caprylic triglyceride (and) Glycerin (and) Ceteareth-25 (and) Sodium Dicocoylethylenediamine PEG-15 Sulfate (and) Sodium Lauroyl Lactylate (and) Behenyl Alcohol (and) Glyceryl Stearate (and) Glyceryl Stearate Citrate (and) Gum Arabic (and) Xanthan Gum (and) Phenoxyethanol (and) Methylparaben (and) Ethylparaben (and) Butylparaben (and) Isobutylparaben

The invention claimed is:

1. A method for the stabilization of a cosmetic composition comprising a cosmetically suitable carrier and/or at least one cosmetic adjuvant and dihydroxyacetone or a derivative of dihydroxyacetone, the method comprising adding to the cosmetic composition metal oxide particles and/or metal hydroxide particles having a primary particle size according to the Scherrer method in the range from 5 nm to 100 nm, wherein said particles have been treated with an organic phosphorus compound selected from: hydroxyalkyldiphosphonic acids; alkylphosphonic acids, which may be substituted by at least one COOH group; aminoalkylenephosphonic acids; or organic phosphoric acid esters or salts thereof.

2. The method of claim 1, wherein the particles have been treated with an organic phosphorus compound selected from phosphoric acid monoalkyl esters or salts thereof.

3. The method of claim 1, wherein the organic phosphorus compound is applied to the particles in an amount of 5 to 20 per cent by weight.

4. The method of claim 1, wherein the metal oxide and/or hydroxide for the particles is selected from the oxides and hydroxides of silicon, titanium, zinc, aluminium, cerium, iron, yttrium or zirconium or mixtures thereof.

5. The method of claim 1, wherein the metal oxide and/or hydroxide for the particles is selected from the oxides and hydroxides of titanium or mixtures thereof.

6. The method of claim 1, wherein before the particles have been treated with the organic phosphorus compound, at least one further coating is applied to the particles comprising: metal oxides or hydroxides of silicon, titanium, zinc, aluminium, cerium, iron, yttrium, manganese or zirconium, where the metal is selected differently to the metal of the base particle; organic acids selected from stearic acid, lauric acid, caproic acid or palmitic acid; polyols; polymers; or organosilicone compounds.

7. The method of claim 1, wherein resulting composition is an aqueous or oily dispersion.

8. The method of claim 1, wherein the resulting composition is a composition which can be applied topically.

9. The method of claim 1, wherein the concentration of the dihydroxyacetone or the dihydroxyacetone derivative in the resulting composition is in the range from 1 to 12 per cent by weight, based on the composition.

10. The method of claim 1, wherein the resulting composition further comprises at least one organic UV filter.

11. The method of claim 1, wherein the particles are titanium dioxide particles.

12. The method of claim 1, wherein the organic phosphorus compound used to treat the particles comprises a phosphoric acid monoalkyl ester selected from phosphoric acid monomethyl ester, phosphoric acid monoethyl ester, phosphoric acid monooctyl ester, phosphoric acid monocetyl ester, phosphoric acid monostearyl ester or phosphoric acid monododecyl ester or salts thereof or mixtures thereof.

13. The method of claim 1, wherein the organic phosphorus compound used to treat the particles comprises phosphoric acid monocetyl ester.

14. The method of claim 1, wherein the metal oxide particles and/or metal hydroxide particles are titanium dioxide particles and the organic phosphorus compound used to treat the particles comprises a phosphoric acid monoalkyl ester selected from phosphoric acid monomethyl ester, phosphoric acid monoethyl ester, phosphoric acid monooctyl ester, phosphoric acid monocetyl ester, phosphoric acid monostearyl ester or phosphoric acid monododecyl ester or salts thereof or mixtures thereof.

15. The method of claim 6, wherein the particles are titanium dioxide particles having a coating of silicon dioxide before the treatment with the organic phosphorus compound and the organic phosphorus compound for the treatment is phosphoric acid monocetyl ester.

16. The method of claim 1, wherein the cosmetic compositions contains at least one cosmetic adjuvant which is a thickener, softener, moisturiser, surface-active agent, emulsifier, preservative, antifoam, perfume, wax, lanolin, propellant, dye or pigment used for cosmetics.

* * * * *